US008173652B2

(12) United States Patent
Hernandez et al.

(10) Patent No.: US 8,173,652 B2
(45) Date of Patent: May 8, 2012

(54) ISOXAZOLE-ISOXAZOLES AND ISOXAZOLE-ISOTHIAZOLES

(75) Inventors: Maria-Clemencia Hernandez, Delemont (CH); Roland Jakob-Roetne, Inzlingen (DE); Matthew C. Lucas, Verona, NJ (US); Andrew Thomas, Binningen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 202 days.

(21) Appl. No.: 12/704,548

(22) Filed: Feb. 12, 2010

(65) Prior Publication Data

US 2010/0210651 A1 Aug. 19, 2010

(30) Foreign Application Priority Data

Feb. 19, 2009 (EP) .................................... 09153162

(51) Int. Cl.
*A61K 31/5377* (2006.01)
*A61K 31/42* (2006.01)
*A61K 31/454* (2006.01)
*C07D 413/06* (2006.01)
*C07D 413/14* (2006.01)

(52) U.S. Cl. ...................... 514/236.8; 514/326; 514/378; 514/380; 544/137; 546/209; 548/243; 548/248

(58) Field of Classification Search .......................... None
See application file for complete search history.

(56) References Cited

U.S. PATENT DOCUMENTS

| | | | |
|---|---|---|---|
| 4,639,266 A | 1/1987 | Heubach et al. | |
| 2003/0055085 A1 | 3/2003 | Wagener et al. | |
| 2004/0006226 A1 | 1/2004 | Ladduwahetty et al. | |

FOREIGN PATENT DOCUMENTS

| | | |
|---|---|---|
| DE | 3525205 | 3/1986 |
| GB | 2336589 | 10/1999 |
| JP | 2007230909 | 9/2007 |
| WO | 0129015 | 4/2001 |
| WO | 0134603 | 5/2001 |
| WO | 0250062 | 6/2002 |
| WO | 02/081474 | 10/2002 |
| WO | 03/004027 | 1/2003 |
| WO | 0315771 | 2/2003 |
| WO | 03044017 | 5/2003 |
| WO | 2004048349 | 6/2004 |
| WO | 2005014553 | 2/2005 |
| WO | 2005118568 | 12/2005 |
| WO | 2005123672 | 12/2005 |
| WO | 2006037480 | 4/2006 |
| WO | 2006044617 | 4/2006 |
| WO | 2006069155 | 6/2006 |
| WO | 2007009275 | 1/2007 |
| WO | 2007/042420 | 4/2007 |
| WO | 2007039389 | 4/2007 |
| WO | 2007052843 | 5/2007 |
| WO | 2007076260 | 7/2007 |
| WO | 2007092751 | 8/2007 |
| WO | 2007/137954 | 12/2007 |
| WO | 2008025539 | 3/2008 |
| WO | 2008025540 | 3/2008 |

OTHER PUBLICATIONS

McNamara et al., Psychobiology (1993), vol. 21, pp. 101-108.
Goodman et al., Tetrahedron (1999) vol. 55 pp. 15067-15070.
Abstract corresponding to JP 2007/230909.
Roy et al., Synthesis, 2003 pp. 1347-1356.
White, et al., Journal of Organic Chemistry (1981), vol. 46(11) pp. 2273-2280.
Shi Shun et al., J Org. Chem. vol. 68 (2003) pp. 6810-6813.
Lam et al., Bioorganic & Medicinal Chemistry Letters (2003) vol. 13(10) pp. 1795-1799.
Wang et al., Journal of Fluorine Chemistry, vol. 111(2) pp. 241-246 (2001).
Hamper et al., J. Agric. Food Chem. (1995), vol. 43, pp. 219-228.
Kumar, et al., Tetrahedron Letters, vol. 47, (2006), p. 1457-1460.
Burke, et al., Journal of Natural Products, 1986, vol. 49, pp. 522-523.
Hormi, Organic Syntheses, vol. 8, p. 247 (1993) & vol. 66, (1988), p. 173.
Andosova et al., Pharmaceutical Chemistry Journal (English Translation), vol. 12, No. 8, 1978, pp. 1019-1022.
Doyle, et al., Journal of the Chem. Society, 1963, pp. 5838-5845.
Anderson, et al., Journal of Organic Chem. vol. 51(6), 1986, pp. 945-947.
Bourbeau et al., Organic Letters, vol. 8(17), 2006, pp. 3670-3680.
Waldo et al., Org. Lett. vol. (7) pp. 5203-5205 (2005).
Seydel et al., J. Med Chem. vol. (19) pp. 483-492 (1976).
Kirk, K. L., J. Org. Chem. vol. (43) pp. 4381-4383 (1978).
Ley et al., Angew Chem, 2003 vol. 115 p. 5558-5606.
Hüttel et al., Liebigs, Ann. Chem. vol. 593, pp. 200-207 (1955) (English language translation attached).
Austin et al., J. Org. Chem. vol. 46, pp. 2280-2286 (1981).
Schlosser et al., Eur. J. Org. Chem. vol. (24), p. 4181-4184 (2002).
Félix et al., J. Org. Chem. 1995, vol. 60 p. 3907-3909.
Otani, et al., Neuroscience Letters, 2005, vol. 381, pp. 108-113.

(Continued)

*Primary Examiner* — Kamal Saeed
(74) *Attorney, Agent, or Firm* — George W. Johnston; Patricia S. Rocha-Tramaloni; Kimberly J. Prior

(57) ABSTRACT

The present invention is concerned with isoxazole-isoxazoles and isoxazole-isothiazoles of formula I, having affinity and selectivity for GABA A α5 receptor, their manufacture, pharmaceutical compositions containing them and their use as cognitive enhancers or for the therapeutic and/or prophylactic treatment of cognitive disorders like Alzheimer's disease.

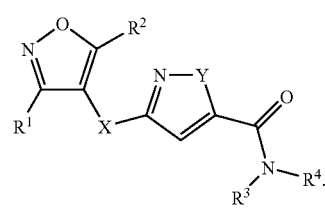

22 Claims, No Drawings

OTHER PUBLICATIONS

Papadimitriou et al., Neuropsychobiology, 2001, vol. 43(3) pp. 141-144.
McCauley et al., Amer. J. Med. Genetics, 2004, 131B, pp. 51-59.
Delong, et al., Autism, 2007, vol. 11(2) pp. 135-147.
Solis-Anez et al., Investigacion Clinica, 2007, vol. 48, pp. 529-541 (English language Abstract attached).
Fernandez et al., Nature Neurosci. 2007, vol. 10, pp. 411-413.
Rueda et al., Neuroscience Letters, 2008, vol. 433, pp. 22-27.
Cui et al., Cell, 2008, vol. 135, pp. 549-560.

ISOXAZOLE-ISOXAZOLES AND ISOXAZOLE-ISOTHIAZOLES

PRIORITY TO RELATED APPLICATION(S)

This application claims the benefit of European Patent Application No. 09153162.4, filed Feb. 19, 2009, which is hereby incorporated by reference in its entirety.

BACKGROUND OF THE INVENTION

Receptors for the major inhibitory neurotransmitter, gamma-aminobutyric acid (GABA), are divided into two main classes: (1) GABA A receptors, which are members of the ligand-gated ion channel superfamily and (2) GABA B receptors, which are members of the G-protein linked receptor family. The GABA A receptor complex which is a membrane-bound heteropentameric protein polymer is composed principally of $\alpha$, $\beta$ and $\gamma$ subunits.

Presently a total number of 21 subunits of the GABA A receptor have been cloned and sequenced. Three types of subunits ($\alpha$, $\beta$ and $\gamma$) are required for the construction of recombinant GABA A receptors which most closely mimic the biochemical, electrophysiological and pharmacological functions of native GABA A receptors obtained from mammalian brain cells. There is strong evidence that the benzodiazepine binding site lies between the $\alpha$ and $\gamma$ subunits. Among the recombinant GABA A receptors, $\alpha 1\beta 2\gamma 2$ mimics many effects of the classical type-I BzR subtypes, whereas $\alpha 2\beta 2\gamma 2$, $\alpha 3\beta 2\gamma 2$ and $\alpha 5\beta 2\gamma 2$ ion channels are termed type-II BzR.

It has been shown by McNamara and Skelton in Psychobiology, 1993, 21:101-108 that the benzodiazepine receptor inverse agonist $\beta$-CCM enhance spatial learning in the Morris watermaze. However, $\beta$-CCM and other conventional benzodiazepine receptor inverse agonists are proconvulsant or convulsant which prevents their use as cognition enhancing agents in humans. In addition, these compounds are non-selective within the GABA A receptor subunits, whereas a GABA A $\alpha 5$ receptor partial or full inverse agonist which is relatively free of activity at GABA A $\alpha 1$ and/or $\alpha 2$ and/or $\alpha 3$ receptor can be used to provide a medicament which is useful for enhancing cognition with reduced or without proconvulsant activity. It is also possible to use GABA A $\alpha 5$ inverse agonists which are not free of activity at GABA A $\alpha 1$ and/or $\alpha 2$ and/or $\alpha 3$ receptor but which are functionally selective for $\alpha 5$ containing subunits. However, inverse agonists which are selective for GABA A $\alpha 5$ subunits and are relatively free of activity at GABA A $\alpha 1$, $\alpha 2$ and $\alpha 3$ receptor are preferred.

Literature has been published to establish the link between GABA A $\alpha 5$ subunits and the therapeutic and/or prophylactic treatment of various diseases of the Central Nervous System, like Neuroscience Letts., 2005, 381, 108-13, Neuropsychobiology, 2001, 43(3), 141-44, Amer. J. Med. Genetics, 2004, 131B, 51-9, Autism 2007, 11(2): 135-47, Investigacion Clinica, 2007, 48, 529-41, Nature Neuroscience, 2007, 10, 411-13, Neuroscience Letts., 2008, 433, 22-7 and Cell 2008, 135, 549-60.

SUMMARY OF THE INVENTION

The present invention provides isoxazole-isoxazoles and isoxazole-isothiazoles having affinity and selectivity for GABA A $\alpha 5$ receptor, their manufacture, pharmaceutical compositions containing them and their use as cognitive enhancers or for the therapeutic and/or prophylactic treatment of cognitive disorders like Alzheimer's disease.

In particular, the present invention provides isoxazoles of formula I.

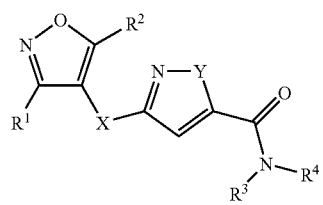

wherein
$R^1$ is lower alkyl, optionally substituted by halogen, cyano, hydroxy, lower-alkoxy or halogen-lower-alkoxy,
  aryl, heteroaryl, cycloalkyl, or heterocyclyl; each of which is optionally substituted by halogen, cyano, hydroxy, lower alkyl, halogen-lower alkyl, cyano-lower alkyl, hydroxy-lower alkyl, lower alkyl-C(=O)OH, lower alkyl-C(=O)O-lower alkyl, lower alkyl-CO—$NR^5R^6$, lower alkyl-$NR^5R^6$, lower-alkoxy-lower alkyl, —CO-lower alkyl, —C(=O)OH, —C(=O)O-lower alkyl, —$CONR^5R^6$, —$NR^5R^6$, lower-alkoxy, halogen-lower-alkoxy, —$SO_2$-lower alkyl, —$SO_2$—$NR^5R^6$, cycloalkyl, phenyloxy or phenyl,
$R^2$ is lower alkyl optionally substituted by halogen, cyano, hydroxy, lower-alkoxy or halogen-lower-alkoxy,
$R^3$ is lower alkyl, optionally substituted by carboxy, halogen or hydroxyl;
  aryl, heteroaryl, cycloalkyl, or heterocyclyl; each of which is optionally substituted by carboxy, halogen, hydroxy or lower alkyl; or
  —$NR^7R^8$,
$R^4$ is H or lower alkyl,
or $R^3$ and $R^4$ together with the nitrogen atom to which they are attached form a heterocyclic ring,
$R^5$ is H or lower alkyl,
$R^6$ is H or lower alkyl,
$R^7$ is H or lower alkyl,
$R^8$ is H or lower alkyl,
Y is O or S, and
X is $CH_2$—O— or —CH=CH—.

DETAILED DESCRIPTION OF THE INVENTION

The present invention provides compounds of formula I per se, pharmaceutical compositions containing them, methods for their manufacture, and the use of compounds of formula I and their pharmaceutically acceptable salts and esters for the therapeutic and/or prophylactic treatment of diseases related to a disorder or condition mediated by the GABA A $\alpha 5$ receptor. Such diseases include chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers.

Preferred indications are cognitive disorders, schizophrenia, positive, negative and/or cognitive symptoms associated with schizophrenia and Alzheimer's disease. Most preferred indications are schizophrenia and Alzheimer's disease. Particularly preferred is the therapeutic and/or prophylactic treatment of Alzheimer's disease.

Furthermore, the invention includes all racemic mixtures, all their corresponding enantiomers, optical isomers and/or tautomers as well as their hydrates, solvates and isotopically-labelled analogues.

Unless otherwise stated, the following terms used in the present application, including the specification and claims, have the definitions given below. It must be noted that, as used in the specification and the appended claims, the singular forms "a", "an," and "the" include plural referents unless the context clearly dictates otherwise.

The term "substituted" means that the specified group or moiety can bear 1, 2, 3, 4, 5 or 6 substituents. Where any group can carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents.

The term "lower alkyl", alone or in combination with other groups, stands for a hydrocarbon radical which is linear or branched, with single or multiple branching, whereby the alkyl group in general contains 1 to 6 carbon atoms, for example, methyl (Me), ethyl (Et), propyl, isopropyl, n-butyl, i-butyl (iso-butyl), 2-butyl (sec-butyl), t-butyl (tert-butyl) and the like. Preferred alkyl groups are groups with 1 to 4 carbon atoms. Most preferred are methyl, ethyl, isopropyl and n-butyl.

The terms "lower alkyl substituted by halogen" and "halogen-lower alkyl" refer to a lower alkyl group substituted by one or multiple halogen atom, for example the following groups: $CF_3$, $CHF_2$, $CH_2F$, $CH_2CF_3$, $CH_2CH_2CF_3$, $CHF_2CF_2$, and the like. Preferred groups are $CF_3$— and $CF_3CH_2$—.

The terms "lower alkyl substituted by carboxy" and "lower alkyl-C(=O)OH" refer to a lower alkyl group substituted by one or multiple carboxy groups, for example the following groups: carboxymethyl-, 2-carboxyethyl- or 2-carboxypropyl-. Preferred group is 2-carboxyethyl-.

The terms "lower alkyl substituted by hydroxy" and "hydroxy-lower alkyl" refer to a lower alkyl group substituted by one or multiple hydroxy groups, for example the following groups: hydroxymethyl-, 2-hydroxyethyl-, 2-hydroxy-1-methyl-ethyl- or 2-hydroxypropyl-. Preferred groups are hydroxy-methyl, 2-hydroxy-1-methyl-ethyl- or 2-hydroxy-ethyl-.

The terms "lower alkyl substituted by cyano" and "cyano-lower alkyl" refer to a lower alkyl group substituted by one or multiple cyano groups, for example the following groups: cyanomethyl-, 2-cyanoethyl-, 2-cyano-1-methyl-ethyl- or 2-cyanopropyl-.

The terms "lower alkyl substituted by lower-alkoxy" and "lower alkoxy-lower alkyl" refer to a lower alkyl group substituted by one or multiple lower alkoxy groups, for example the following groups: MeO-Me-, 2-MeO-Et-, 2-EtO-1-MeO-Et- or 2-EtO-propyl-.

The term "lower alkyl substituted by halogen-lower-alkoxy" refers to a lower alkyl group substituted by one or multiple halogen-lower alkoxy groups, for example the following groups: Cl-MeO-Me-, F-MeO-Me-, or Cl-MeO-Et-.

The term "lower alkyl-C(=O)O-lower alkyl" refers to a lower alkyl group substituted by one or multiple lower alkyl-C(=O)O, for example the following group: Me-C(=O)O-Me-.

The term "lower alkyl-CO—NR$^5$R$^6$" refers to a lower alkyl group substituted by one or multiple —CO—NR$^5$R$^6$, for example the following group: $NH_2$—CO-Me-.

The term "lower alkyl-NR$^5$R$^6$" refers to a lower alkyl group substituted by one or multiple —NR$^5$R$^6$, for example the following group: $NH_2$Me-.

The term "—CO-lower alkyl" refers to a lower alkyl group linked via a CO, for example the following group: Me-CO—.

The term "—C(=O)O-lower alkyl" refers to a lower alkyl group linked via a —C(=O)O—, for example the following group: Me-C(=O)O—.

The term "—SO$_2$-lower alkyl" refers to a lower alkyl group linked via a —SO$_2$, for example the following group: Me-SO$_2$—.

The term "lower alkoxy" stands for a "—O-lower alkyl" radical which is linear, cyclic or branched, with single or multiple branching, whereby the alkyl group in general comprises 1 to 6 carbon atoms, for example, methoxy (OMe), ethoxy (OEt), propoxy, isopropoxy, n-butoxy, i-butoxy (iso-butoxy), 2-butoxy (sec-butoxy), t-butoxy (tert-butoxy) and the like. Preferred alkoxy groups are groups with 1 to 4 carbon atoms. Most preferred are methoxy, ethoxy, propoxy and n-butoxy.

The term "halogen-lower alkoxy" refers to a lower alkoxy group substituted by one or multiple halogen atoms, for example the following groups: F-MeO—.

The term "halogen" denotes chlorine (Cl), iodine (I), fluorine (F) and bromine (Br). Preferred halogen is fluorine.

The term "aryl" refers to an aromatic carbocyclic group comprising 6 to 14, preferably 6 to 10, carbon atoms and having at least one aromatic ring or multiple condensed rings in which at least one ring is aromatic, for example phenyl (Ph), benzyl, naphthyl, biphenyl or indanyl. Preferred aryl group is phenyl.

The term "aryl substituted by" refers to an aryl group that is substituted by one or multiple substituents, whereby substitution at each ring atom individually is possible, selected from carboxy, halogen, hydroxy or lower alkyl. Preferred substituents are F, Cl, Me or $CF_3$. Preferred "aryl substituted by is 4-fluoro-phenyl.

The term "heteroaryl" refers to a cyclic aromatic group having a single 4 to 8 membered ring or multiple condensed rings comprising 6 to 14, more preferably 6 to 10, ring atoms and containing at least one heteroatom selected from N, O and S, within at least one ring, the number of N atoms being 0, 1, 2 or 3 and the number of O and S atoms each being 0, 1 or 2; in which group at least one heterocyclic ring is aromatic. Examples of such groups include pyrrolyl, thienyl, furyl, pyrazolyl, imidazolyl, triazolyl, tetrazolyl, thiazolyl, isothiazolyl, oxazolyl, isoxazolyl, pyridinyl, pyrimidinyl, pyrazinyl, pyridazinyl, indolyl, indazolyl, quinolinyl, isoquinolinyl, benzofuryl, benzothiazolyl, benzotriazolyl, benzoimidazolyl, benzooxazinyl, benzothiazinyl, benzothienyl and the like. Preferred heteroaryl group is pyridinyl.

The term "heteroaryl substituted by" refers to a heteroaryl group that is substituted by one or multiple substituents, whereby substitution at each ring atom individually is possible, selected from carboxy, halogen, hydroxy and lower alkyl. Preferred substituents are F or Me. Preferred "substituted heteroaryl" is 3-fluoro-pyridinyl.

The terms "heterocyclyl" or "heterocyclic ring" refer to a 4 to 8-membered ring containing at least one heteroatom, such as N, O or S, the number of N atoms being 0, 1, 2 or 3 and the number of O and S atoms each being 0, 1 or 2, which ring can be part of a multiple condensed ring-system. Examples of such cycloheteroalkyl groups include pyrrolidinyl, tetrahydrofuryl, tetrahydrothienyl, tetrahydropyridinyl, tetrahydropyryl, azetidinyl, thiazolidinyl, oxazolidinyl, piperidinyl, morpholinyl, thiomorpholinyl, piperazinyl, azepanyl, diazepanyl, oxazepanyl and the like. Preferred cycloheteroalkyl groups are morpholinyl, tetrahydrofuryl, tetrahydropyryl pyrrolidinyl and piperidinyl.

The term "heterocyclyl substituted by" refers to a heterocyclyl which is substituted by one or multiple substituents, whereby substitution at each ring atom individually is possible, selected from carboxy, halogen, hydroxy or lower alkyl.

The term "cycloalkyl" refers to a 3 to 8 membered alicyclic carbon ring, for example cyclopropyl, cyclobutyl, cyclopentyl, cyclohexyl, cycloheptyl or cyclooctyl.

The term "cycloalkyl substituted by" refers to a cycloalkyl group that is substituted by one or multiple substituents, whereby substitution at each ring atom individually is possible, selected from carboxy, halogen, hydroxy or lower alkyl.

The term "hydroxy" refers to the group —OH.

The term "cyano" refers to the group —C≡N.

The term "carboxy" refers to the group C—(C=O)—O—.

The term "phenyloxy" refers to the group —O—$C_6H_5$.

The terms "pharmaceutically acceptable salts" and "pharmaceutically active salts" refer to salts that are, suitable for use in contact with the tissues of humans and lower animals without undue toxicity, irritation, allergic response, and the like, and are commensurate with a reasonable benefit-risk ratio. Examples of suitable salts with inorganic and organic acids are, but are not limited to, hydrochloric acid, nitric acid, phosphoric acid, sulphuric acid, citric acid, formic acid, fumaric acid, maleic acid, lactic acid, malic acid, acetic acid, succinic acid, tartaric acid, methane-sulfonic acid, p-toluene-sulphonic acid, trifluoroacetic acid and the like.

The terms "pharmaceutically acceptable esters" and "pharmaceutically active esters" refer to a conventionally esterified compound having a carboxyl group, which esters retain the biological effectiveness and properties of the respective compounds of formula I and are cleaved in vivo (in the organism) to the corresponding active carboxylic acid. Examples of ester groups which are cleaved (in this case hydrolyzed) in vivo to the corresponding carboxylic acids are those in which the cleaved hydrogen is replaced with-lower alkyl which is optionally substituted with heterocyclyl, cycloalkyl, etc. Examples of substituted lower alkyl esters are those in which-lower alkyl is substituted with pyrrolidine, piperidine, morpholine, N-methylpiperazine, etc. Furthermore, the term "pharmaceutically acceptable esters" refer to a conventionally esterified compound having a hydroxy group, which esters retain the biological effectiveness and properties of the respective compounds of formula I and are cleaved in vivo (in the organism) to the corresponding compound of formula I. The hydroxy compounds can be converted to the corresponding esters with inorganic or organic acids such as, nitric acid, sulphuric acid, phosphoric acid, citric acid, formic acid, maleic acid, acetic acid, succinic acid, tartaric acid, methane-sulphonic acid, p-toluenesulphonic acid and the like, which acids are non-toxic to living organisms.

"Therapeutically effective amount" means an amount that is effective to prevent, alleviate or ameliorate symptoms of disease or prolong the survival of the subject being treated.

The conversion into pharmaceutically acceptable esters of compounds of formula I bearing a carboxy group can be carried out e.g. by treatment of a suitable carboxy group with a suitable alcohol using e.g. a condensating reagent such as benzotriazol-1-yloxytris(dimethylamino)-phosphonium hexafluorophosphate (BOP), N,N-dicylohexyl-carbodiimide (DCC), N-(3-dimethylaminopropyl)-N'-ethylcarbodiimide hydrochloride (EDCI) or O-(1,2-dihydro-2-oxo-1-pyridyl)-N,N,N,N-tetra-methyluronium-tetrafluoro-borate (TPTU), or by direct reaction with a suitable alcohol under acidic conditions, as for example in the presence of a strong mineral acid like hydrochloric acid, sulphuric acid and the like. The conversion into pharmaceutically acceptable esters of compounds of formula I bearing a hydroxy group can be carried out with suitable acids by analogous methods.

The term "solvates" refers to a complex of the respective compound that contains either stoichiometric or non-stoichiometric amounts of a solvent, which have been included with a defined molar ratio in the structure. Such solvents for the purpose of the invention may not interfere with the biological activity of the solute. "Solvates" are called "hydrates" in case the included solvent is water. The compound of formula I and pharmaceutically acceptable salts thereof can exist in the form of a hydrate or a solvate, and such a hydrate and solvate are also encompassed in the present invention. Examples thereof include hydrate, dihydrochloride dihydrate, and the like.

The word "comprise" and variations of the word, such as "comprising" and "comprises" is not intended to exclude other additives, components, integers or steps.

The terms "pharmaceutically acceptable carrier" and "pharmaceutically acceptable auxiliary substance" refer to carriers and auxiliary substances such as diluents or excipients that are compatible with the other ingredients of the formulation and not deleterious to the recipient thereof.

The term "mammal" refers to any member of the mammalian class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. Preferred mammals are humans.

The compounds of formula I can contain one or more asymmetric centres and can therefore occur as racemates, racemic mixtures, single enantiomers, diastereomeric mixtures and individual diastereomers. Additional asymmetric centres can be present depending upon the nature of the various substituents on the molecule. Each such asymmetric centre will independently produce two optical isomers and it is intended that all of the possible optical isomers and diastereomers in mixtures and as pure or partially purified compounds are included within this invention. The present invention is meant to comprehend all such isomeric forms of these compounds. The independent syntheses of these diastereomers or their chromatographic separations can be achieved as known in the art by appropriate modification of the methodology disclosed herein. Their absolute stereochemistry can be determined by the x-ray crystallography of crystalline products or crystalline intermediates which are derivatized, if necessary, with a reagent containing an asymmetric centre of known absolute configuration. If desired, racemic mixtures of the compounds can be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

In the embodiments, where optically pure enantiomers are provided, the term "optically pure enantiomer" means that the compound contains >90% of the desired isomer by weight, preferably >95% of the desired isomer by weight, or more preferably >99% of the desired isomer by weight, said weight percent based upon the total weight of the isomer(s) of the compound. Chirally pure or chirally enriched compounds can be prepared by chirally selective synthesis or by separation of enantiomers. The separation of enantiomers can be carried out on the final product or alternatively on a suitable intermediate. Separation of enantiomers can be performed by chromatography on a chiral stationary phase, e.g. on a Chiralcel OD or a Chiralpak AD column, with an eluent compatible with the stationary phase like a hydrocarbon as pentanes, hexanes or heptanes mixed with a low alcohol as ethanol, n-propanol or isopropanol, preferred are heptane/isopropanol or heptane/ethanol mixtures.

Isotopically-labelled compounds of formula I, including compounds of formula I isotopically-labelled to be detectable by PET or SPECT, also fall within the scope of the invention. The same applies to compounds of formula I labelled with [$^{13}$C]—, [$^{14}$C]—, [$^{3}$H]—, [$^{18}$F]—, [$^{125}$I]— or other isotopically enriched atoms, suitable for receptor binding or metabolism studies.

The term "pharmaceutical composition" encompasses a product comprising specified ingredients in pre-determined amounts or proportions, as well as any product that results, directly or indirectly, from combining specified ingredients in specified amounts. Preferably it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The following table lists abbreviations used within the present document.

TABLE 1

| | abbreviations |
|---|---|
| brine | water saturated with sodium chloride |
| BuLi | butyl lithium |
| DCM | dichloromethane |
| DIAD | diisopropyl azodicarboxylate |
| DEAD | diethyl azodicarboxylate |
| DMF | N,N-dimethylformamide |
| EI | electron ionization |
| HCl | hydrochloride |
| KCl, CaCl$_2$, MgCl$_2$ | potassium chloride, calcium chloride, magnesium chloride |
| LiOH, NaOH | lithium hydroxide, sodium hydroxide |
| Me$_3$Al | trimethylaluminium |
| MeOH, EtOH | methanol, ethanol |
| MS | mass spectrum |
| NMO | N-Methylmorpholin-N-oxid |
| on | overnight |
| PCC | pyridinium chlorochromate |
| PET | Positrons-Emissions-Computer-Tomography |
| rt | room temperature |
| Seignette's salt | potassium sodium tartrate |
| SPECT | Single-Photon-Emissions-Computer-Tomography |
| TBD | 1,5,7-triazabicyclo[4.4.0]dec-5-ene |
| THF | tetrahydrofuran |
| Tris | tris(hydroxymethyl)-aminomethane |

The invention also provides pharmaceutical compositions, methods of using, and methods of preparing the aforementioned compounds.

While the present invention has been described with reference to the specific embodiments thereof, it should be understood by those skilled in the art that various changes can be made and equivalents can be substituted without departing from the true spirit and scope of the invention. In addition, many modifications can be made to adapt a particular situation, material, composition of matter, process, process step or steps, to the objective spirit and scope of the present invention. All such modifications are intended to be within the scope of the claims appended hereto. All separate embodiments can be combined.

One embodiment of the invention provides compounds of formula I

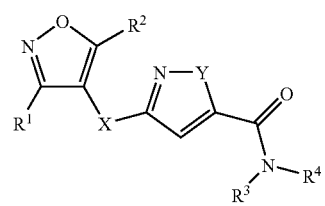

wherein
$R^1$ is lower alkyl, optionally substituted by halogen, cyano, hydroxy, lower-alkoxy or halogen-lower-alkoxy,
aryl, heteroaryl, cycloalkyl, or heterocyclyl; each of which is optionally substituted by halogen, cyano, hydroxy, lower alkyl, halogen-lower alkyl, cyano-lower alkyl, hydroxy-lower alkyl, lower alkyl-C(═O)OH, lower alkyl-C(═O)O-lower alkyl, lower alkyl-CO—NR$^5$R$^6$, lower alkyl-NR$^5$R$^6$, lower-alkoxy-lower alkyl, —CO-lower alkyl, —C(═O)OH, —C(═O)O-lower alkyl, —CONR$^5$R$^6$, —NR$^5$R$^6$, lower-alkoxy, halogen-lower-alkoxy, —SO$_2$-lower alkyl, —SO$_2$—NR$^5$R$^6$, cycloalkyl, phenyloxy or phenyl,
$R^2$ is lower alkyl optionally substituted by halogen, cyano, hydroxy, lower-alkoxy or halogen-lower-alkoxy,
$R^3$ is lower alkyl, optionally substituted by carboxy, halogen or hydroxyl;
aryl, heteroaryl, cycloalkyl, or heterocyclyl; each of which is optionally substituted by carboxy, halogen, hydroxy or lower alkyl; or
—NR$^7$R$^8$,
$R^4$ is H or lower alkyl,
or $R^3$ and $R^4$ together with the nitrogen atom to which they are attached form a heterocyclic ring,
$R^5$ is H or lower alkyl,
$R^6$ is H or lower alkyl,
$R^7$ is H or lower alkyl,
$R^8$ is H or lower alkyl,
Y is O or S, and
X is CH$_2$—O— or —CH═CH—,
or pharmaceutically active salts or esters thereof.

One further embodiment of the invention provides compounds wherein Y is O.

One further embodiment of the invention provides compounds wherein Y is S.

One further embodiment of the invention provides compounds wherein X is —CH$_2$—O—.

One further embodiment of the invention provides compounds of formula I'

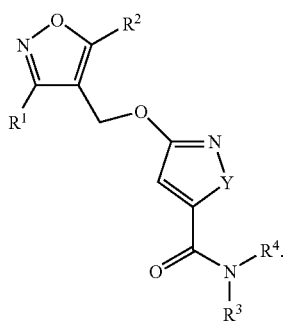

One further embodiment of the invention provides compounds wherein X is —CH=CH—.

One further embodiment of the invention provides compounds wherein $R^2$ is lower alkyl optionally substituted by halogen, cyano, hydroxy, lower-alkoxy or halogen-lower-alkoxy.

One further embodiment of the invention provides compounds wherein $R^2$ is lower alkyl substituted by halogen.

One further embodiment of the invention provides compounds wherein $R^2$ is lower alkyl substituted by cyano.

One further embodiment of the invention provides compounds wherein $R^2$ is lower alkyl substituted by hydroxyl.

One further embodiment of the invention provides compounds wherein $R^2$ is lower alkyl substituted by lower-alkoxy.

One further embodiment of the invention provides compounds wherein $R^2$ is lower alkyl substituted by halogen-lower-alkoxy.

One further embodiment of the invention provides compounds wherein $R^2$ is unsubstituted lower alkyl.

One further embodiment of the invention provides compounds wherein $R^2$ is Me.

One further embodiment of the invention provides compounds wherein $R^2$ is hydroxy-lower alkyl.

One further embodiment of the invention provides compounds wherein $R^1$ is lower alkyl, optionally substituted by halogen, cyano, hydroxy, lower-alkoxy or halogen-lower-alkoxy; aryl, heteroaryl, cycloalkyl, heterocyclyl; each of which is optionally substituted by halogen, cyano, hydroxy, lower alkyl, halogen-lower alkyl, cyano-lower alkyl, hydroxy-lower alkyl, lower alkyl-C(=O)OH, lower alkyl-C(=O)O-lower alkyl, lower alkyl-CO—$NR^5R^6$, lower alkyl-$NR^5R^6$, lower-alkoxy-lower alkyl, —CO-lower alkyl, —C(=O)OH, —C(=O)O-lower alkyl, —CONR$^5R^6$, —$NR^5R^6$, lower-alkoxy, halogen-lower-alkoxy, —SO$_2$-lower alkyl, —SO$_2$—$NR^5R^6$, cycloalkyl, phenyloxy or phenyl.

One further embodiment of the invention provides compounds wherein $R^1$ is lower alkyl, aryl, aryl substituted by halogen, heteroaryl, or heteroaryl substituted by halogen.

One further embodiment of the invention provides compounds wherein $R^1$ is n-butyl, Ph, 4-fluoro-Ph, pyridinyl or 3-fluoro-pyridinyl.

One further embodiment of the invention provides compounds wherein $R^1$ is lower alkyl, optionally substituted by halogen, cyano, hydroxy, lower-alkoxy or halogen-lower-alkoxy.

One further embodiment of the invention provides compounds wherein $R^1$ is lower alkyl, substituted by halogen.

One further embodiment of the invention provides compounds wherein $R^1$ is lower alkyl, substituted by cyano.

One further embodiment of the invention provides compounds wherein $R^1$ is lower alkyl, substituted by hydroxy.

One further embodiment of the invention provides compounds wherein $R^1$ is lower alkyl, substituted by lower-alkoxy.

One further embodiment of the invention provides compounds wherein $R^1$ is lower alkyl, substituted by halogen-lower-alkoxy.

One further embodiment of the invention provides compounds wherein $R^1$ is unsubstituted lower alkyl.

One further embodiment of the invention provides compounds wherein $R^1$ is n-butyl.

One further embodiment of the invention provides compounds wherein $R^1$ is aryl optionally substituted by halogen, cyano, hydroxy, lower alkyl, halogen-lower alkyl, cyano-lower alkyl, hydroxy-lower alkyl, lower alkyl-C(=O)OH, lower alkyl-C(=O)O-lower alkyl, lower alkyl-CO—$NR^5R^6$, lower alkyl-$NR^5R^6$, lower-alkoxy-lower alkyl, —CO-lower alkyl, —C(=O)OH, —C(=O)O-lower alkyl, —CONR$^5R^6$, —$NR^5R^6$, lower-alkoxy, halogen-lower-alkoxy, —SO$_2$-lower alkyl, —SO$_2$—$NR^5R^6$, cycloalkyl, phenyloxy or phenyl.

One further embodiment of the invention provides compounds wherein $R^1$ is aryl substituted by halogen.

One further embodiment of the invention provides compounds wherein $R^1$ is 4-fluoro-Ph.

One further embodiment of the invention provides compounds wherein $R^1$ is unsubstituted aryl.

One further embodiment of the invention provides compounds wherein $R^1$ is Ph.

One further embodiment of the invention provides compounds wherein $R^1$ heteroaryl, optionally substituted by halogen, cyano, hydroxy, lower alkyl, halogen-lower alkyl, cyano-lower alkyl, hydroxy-lower alkyl, lower alkyl-C(=O)OH, lower alkyl-C(=O)O-lower alkyl, lower alkyl-CO—$NR^5R^6$, lower alkyl-$NR^5R^6$, lower-alkoxy-lower alkyl, —CO-lower alkyl, —C(=O)OH, —C(=O)O-lower alkyl, —CONR$^5R^6$, —$NR^5R^6$, lower-alkoxy, halogen-lower-alkoxy, —SO$_2$-lower alkyl, —SO$_2$—$NR^5R^6$, cycloalkyl, phenyloxy or phenyl.

One further embodiment of the invention provides compounds wherein $R^1$ is heteroaryl substituted by halogen.

One further embodiment of the invention provides compounds wherein $R^1$ is 3-fluoro-pyridinyl.

One further embodiment of the invention provides compounds wherein $R^1$ is unsubstituted heteroaryl.

One further embodiment of the invention provides compounds wherein $R^1$ is pyridinyl.

One further embodiment of the invention provides compounds wherein $R^1$ is cycloalkyl, optionally substituted by halogen, cyano, hydroxy, lower alkyl, halogen-lower alkyl, cyano-lower alkyl, hydroxy-lower alkyl, lower alkyl-C(=O)OH, lower alkyl-C(=O)O-lower alkyl, lower alkyl-CO—$NR^5R^6$, lower alkyl-$NR^5R^6$, lower-alkoxy-lower alkyl, —CO-lower alkyl, —C(=O)OH, —C(=O)O-lower alkyl, —CONR$^5R^6$, —$NR^5R^6$, lower-alkoxy, halogen-lower-alkoxy, —SO$_2$-lower alkyl, —SO$_2$—$NR^5R^6$, cycloalkyl, phenyloxy or phenyl.

One further embodiment of the invention provides compounds wherein $R^1$ is unsubstituted cycloalkyl.

One further embodiment of the invention provides compounds wherein $R^1$ is heterocyclyl, optionally substituted by halogen, cyano, hydroxy, lower alkyl, halogen-lower alkyl, cyano-lower alkyl, hydroxy-lower alkyl, lower alkyl-C(=O) OH, lower alkyl-C(=O)O-lower alkyl, lower alkyl-CO—

NR$^5$R$^6$, lower alkyl-NR$^5$R$^6$, lower-alkoxy-lower alkyl, —CO-lower alkyl, —C(=O)OH, —C(=O)O-lower alkyl, —CONR$^5$R$^6$, —NR$^5$R$^6$, lower-alkoxy, halogen-lower-alkoxy, —SO$_2$-lower alkyl, —SO$_2$—NR$^5$R$^6$, cycloalkyl, phenyloxy or phenyl.

One further embodiment of the invention provides compounds wherein R$^1$ is unsubstituted heterocyclyl.

One further embodiment of the invention provides compounds wherein R$^3$ is lower alkyl, aryl, heteroaryl, cycloalkyl, heterocyclyl; each optionally substituted by carboxy, halogen, hydroxy or lower alkyl; or —NR$^7$R$^8$, with R$^7$, R$^8$ each being lower alkyl or H; or R$^3$ and R$^4$ together with the nitrogen atom to which they are attached form a heterocyclic ring.

One further embodiment of the invention provides compounds wherein R$^3$ is lower alkyl, lower alkyl substituted with hydroxyl, lower alkyl substituted with carboxy, lower alkyl substituted with halogen, heterocyclyl; or —NR$^7$R$^8$, with R$^7$, R$^8$ being lower alkyl;

One further embodiment of the invention provides compounds wherein R$^3$ is 2,2,2-trifluoro-ethyl-, 2-carboxyethyl-, 2-hydroxy-1-methyl-ethyl-, 2-hydroxy-ethyl-, 3-tetrahydrofuranyl-, 4-tetrahydropyranyl-, isopropyl-, (CH$_3$)$_2$N—, piperidinyl, pyrrolidinyl or morpholino.

One further embodiment of the invention provides compounds wherein or R$^3$ and R$^4$ form together with the nitrogen to which they are attached a heterocyclic ring.

One further embodiment of the invention provides compounds wherein R$^3$ and R$^4$ form together with the nitrogen to which they are attached 2-oxa-6-aza-spiro[3.3]hept-6-yl.

One further embodiment of the invention provides compounds wherein R$^3$ is unsubstituted heterocyclyl.

One further embodiment of the invention provides compounds wherein R$^3$ is 3-tetrahydrofuranyl-.

One further embodiment of the invention provides compounds wherein R$^3$ is 4-tetrahydropyranyl-.

One further embodiment of the invention provides compounds wherein R$^3$ is piperidinyl.

One further embodiment of the invention provides compounds wherein R$^3$ is pyrrolidinyl.

One further embodiment of the invention provides compounds wherein R$^3$ is morpholino.

One further embodiment of the invention provides compounds wherein R$^3$ is lower alkyl, optionally substituted by carboxy, halogen, hydroxy or lower alkyl.

One further embodiment of the invention provides compounds wherein R$^3$ is 2,2,2-trifluoro-ethyl-.

One further embodiment of the invention provides compounds wherein R$^3$ is 2-carboxyethyl-.

One further embodiment of the invention provides compounds wherein R$^3$ is 2-hydroxy-1-methyl-ethyl-.

One further embodiment of the invention provides compounds wherein R$^3$ is 2-hydroxy-ethyl-.

One further embodiment of the invention provides compounds wherein R$^3$ is unsubstituted lower alkyl.

One further embodiment of the invention provides compounds wherein R$^3$ is isopropyl-.

One further embodiment of the invention provides compounds wherein R$^3$ is methyl.

One further embodiment of the invention provides compounds wherein R$^3$ is aryl, optionally substituted by carboxy, halogen, hydroxy or lower alkyl.

One further embodiment of the invention provides compounds wherein R$^3$ is unsubstituted aryl.

One further embodiment of the invention provides compounds wherein R$^3$ is heteroaryl, optionally substituted by carboxy, halogen, hydroxy or lower alkyl.

One further embodiment of the invention provides compounds wherein R$^3$ is unsubstituted heteroaryl.

One further embodiment of the invention provides compounds wherein R$^3$ is cycloalkyl, optionally substituted by carboxy, halogen, hydroxy or lower alkyl.

One further embodiment of the invention provides compounds wherein R$^3$ is unsubstituted cycloalkyl.

One further embodiment of the invention provides compounds wherein R$^3$ is heterocyclyl, optionally substituted by carboxy, halogen, hydroxy or lower alkyl.

One further embodiment of the invention provides compounds wherein R$^3$ is —NR$^7$R$^8$, with R$^7$, R$^8$ each independently being lower alkyl or H.

One further embodiment of the invention provides compounds wherein R$^3$ is —NR$^7$R$^8$, with R$^7$, R$^8$ each independently being H.

One further embodiment of the invention provides compounds wherein R$^3$ is —NR$^7$R$^8$, with R$^7$, R$^8$ each independently being lower alkyl.

One further embodiment of the invention provides compounds wherein R$^3$ is (CH$_3$)$_2$N—.

One further embodiment of the invention provides compounds wherein R$^4$ is H.

One further embodiment of the invention provides compounds wherein R$^4$ is lower alkyl.

One further embodiment of the invention provides compounds wherein R is methyl.

One further embodiment of the invention provides compounds wherein R is ethyl.

One further embodiment of the invention provides compounds wherein R$^5$ is H.

One further embodiment of the invention provides compounds wherein R$^6$ is H.

One further embodiment of the invention provides compounds wherein R$^7$ is Me.

One further embodiment of the invention provides compounds wherein R$^8$ is Me.

One further embodiment of the invention provides compounds, selected from the group consisting of 3-[(E)-2-(3-Butyl-5-methyl-isoxazol-4-yl)-vinyl]-isoxazole-5-carboxylic acid (2-hydroxy-ethyl)-amide,
- 3-(5-Methyl-3-phenyl-isoxazol-4-ylmethoxy)-isoxazole-5-carboxylic acid isopropylamide, 3-(5-Methyl-3-phenyl-isoxazol-4-ylmethoxy)-isoxazole-5-carboxylic acid (tetrahydro-furan-3-yl)-amide,
- 3-(5-Methyl-3-phenyl-isoxazol-4-ylmethoxy)-isoxazole-5-carboxylic acid (2-hydroxy-ethyl)-amide,
- 3-(5-Methyl-3-phenyl-isoxazol-4-ylmethoxy)-isoxazole-5-carboxylic acid (2-hydroxy-1-methyl-ethyl)-amide,
- Acetic acid 2-{[3-(5-methyl-3-phenyl-isoxazol-4-ylmethoxy)-isoxazole-5-carbonyl]-amino}-ethyl ester,
- 3-(5-Methyl-3-phenyl-isoxazol-4-ylmethoxy)-isoxazole-5-carboxylic acid ((S)-2-hydroxy-1-methyl-ethyl)-amide,
- 3-(5-Methyl-3-phenyl-isoxazol-4-ylmethoxy)-isoxazole-5-carboxylic acid ((R)-2-hydroxy-1-methyl-ethyl)-amide,
- 3-(5-Methyl-3-phenyl-isoxazol-4-ylmethoxy)-isoxazole-5-carboxylic acid N',N'-dimethyl-hydrazide,
- 3-(5-Methyl-3-phenyl-isoxazol-4-ylmethoxy)-isoxazole-5-carboxylic acid piperidin-1-ylamide,
- 3-(5-Methyl-3-phenyl-isoxazol-4-ylmethoxy)-isoxazole-5-carboxylic acid pyrrolidin-1-ylamide,
- 3-(5-Methyl-3-phenyl-isoxazol-4-ylmethoxy)-isoxazole-5-carboxylic acid morpholin-4-ylamide,
- 3-(5-Methyl-3-pyridin-2-yl-isoxazol-4-ylmethoxy)-isoxazole-5-carboxylic acid isopropylamide,
- 3-(5-Methyl-3-pyridin-2-yl-isoxazol-4-ylmethoxy)-isoxazole-5-carboxylic acid (2-hydroxy-ethyl)-amide, 3-(5-Methyl-3-pyridin-2-yl-isoxazol-4-ylmethoxy)-isoxazole-5-carboxylic acid (tetrahydro-furan-3-yl)-amide,
3-(5-Methyl-3-pyridin-2-yl-isoxazol-4-ylmethoxy)-isoxazole-5-carboxylic acid (2,2,2-trifluoro-ethyl)-amide,
3-(5-Methyl-3-pyridin-2-yl-isoxazol-4-ylmethoxy)-isoxazole-5-carboxylic acid N',N'-dimethyl-hydrazide,
3-(5-Methyl-3-pyridin-2-yl-isoxazol-4-ylmethoxy)-isoxazole-5-carboxylic acid morpholin-4-ylamide,
3-(5-Methyl-3-pyridin-2-yl-isoxazol-4-ylmethoxy)-isoxazole-5-carboxylic acid piperidin-1-ylamide,
3-(5-Methyl-3-pyridin-2-yl-isoxazol-4-ylmethoxy)-isoxazole-5-carboxylic acid pyrrolidin-1-ylamide,
3-[3-(5-Fluoro-pyridin-2-yl)-5-methyl-isoxazol-4-ylmethoxy]-isoxazole-5-carboxylic acid isopropylamide,
3-[3-(5-Fluoro-pyridin-2-yl)-5-methyl-isoxazol-4-ylmethoxy]-isoxazole-5-carboxylic acid (2-hydroxy-ethyl)-amide,
3-(3-Butyl-5-methyl-isoxazol-4-ylmethoxy)-isoxazole-5-carboxylic acid (2-hydroxy-ethyl)-amide,
3-(3-Butyl-5-methyl-isoxazol-4-ylmethoxy)-isoxazole-5-carboxylic acid (2-hydroxy-1-methyl-ethyl)-amide,
3-(3-Butyl-5-methyl-isoxazol-4-ylmethoxy)-isoxazole-5-carboxylic acid ((S)-2-hydroxy-1-methyl-ethyl)-amide,
3-(3-Butyl-5-methyl-isoxazol-4-ylmethoxy)-isoxazole-5-carboxylic acid ((R)-2-hydroxy-1-methyl-ethyl)-amide,
3-(3-Butyl-5-methyl-isoxazol-4-ylmethoxy)-isoxazole-5-carboxylic acid isopropylamide,
3-(3-Butyl-5-methyl-isoxazol-4-ylmethoxy)-isoxazole-5-carboxylic acid (tetrahydro-furan-3(S)-yl)-amide,
3-(3-Butyl-5-methyl-isoxazol-4-ylmethoxy)-isoxazole-5-carboxylic acid (tetrahydro-furan-3(R)-yl)-amide
3-(3-Butyl-5-methyl-isoxazol-4-ylmethoxy)-isoxazole-5-carboxylic acid (tetrahydro-furan-3-yl)-amide
3-(3-Butyl-5-methyl-isoxazol-4-ylmethoxy)-isoxazole-5-carboxylic acid N',N'-dimethyl-hydrazide,
3-(3-Butyl-5-methyl-isoxazol-4-ylmethoxy)-isoxazole-5-carboxylic acid morpholin-4-ylamide,
3-(5-Methyl-3-phenyl-isoxazol-4-ylmethoxy)-isothiazole-5-carboxylic acid isopropylamide,
3-(5-Methyl-3-phenyl-isoxazol-4-ylmethoxy)-isothiazole-5-carboxylic acid (2-hydroxy-ethyl)-amide,
3-(5-Methyl-3-pyridin-2-yl-isoxazol-4-ylmethoxy)-isothiazole-5-carboxylic acid isopropylamide,
3-(5-Methyl-3-pyridin-2-yl-isoxazol-4-ylmethoxy)-isothiazole-5-carboxylic acid (2-hydroxy-ethyl)-amide,
3-[3-(5-Fluoro-pyridin-2-yl)-5-methyl-isoxazol-4-ylmethoxy]-isothiazole-5-carboxylic acid isopropylamide,
3-[3-(5-Fluoro-pyridin-2-yl)-5-methyl-isoxazol-4-ylmethoxy]-isothiazole-5-carboxylic acid (2-hydroxy-ethyl)-amide,
3-[3-(5-Fluoro-pyridin-2-yl)-5-methyl-isoxazol-4-ylmethoxy]-isothiazole-5-carboxylic acid (tetrahydro-furan-3-yl)-amide,
3-(3-Butyl-5-methyl-isoxazol-4-ylmethoxy)-isothiazole-5-carboxylic acid (tetrahydro-furan-3-yl)-amide,
{3-[3-(4-Fluoro-phenyl)-5-methyl-isoxazol-4-ylmethoxy]-isoxazol-5-yl}-(2-oxa-6-aza-spiro[3.3]hept-6-yl)-methanone
3-[3-(4-Fluoro-phenyl)-5-hydroxymethyl-isoxazol-4-ylmethoxy]-isoxazole-5-carboxylic acid isopropylamide
3-[3-(4-Fluoro-phenyl)-5-hydroxymethyl-isoxazol-4-ylmethoxy]-isoxazole-5-carboxylic acid (tetrahydro-pyran-4-yl)-amide, and
3-[3-(4-Fluoro-phenyl)-5-hydroxymethyl-isoxazol-4-ylmethoxy]-isoxazole-5-carboxylic acid (2,2,2-trifluoro-ethyl)-amide,
or pharmaceutically active salts or esters thereof.

One further embodiment of the invention provides compounds, selected from the group consisting of 3-(5-Methyl-3-pyridin-2-yl-isoxazol-4-ylmethoxy)-isoxazole-5-carboxylic acid (tetrahydro-furan-3-yl)-amide,
3-[3-(5-Fluoro-pyridin-2-yl)-5-methyl-isoxazol-4-ylmethoxy]-isoxazole-5-carboxylic acid isopropylamide,
3-(5-Methyl-3-pyridin-2-yl-isoxazol-4-ylmethoxy)-isoxazole-5-carboxylic acid morpholin-4-ylamide,
3-[3-(5-Fluoro-pyridin-2-yl)-5-methyl-isoxazol-4-ylmethoxy]-isoxazole-5-carboxylic acid (2-hydroxy-ethyl)-amide,
3-(5-Methyl-3-pyridin-2-yl-isoxazol-4-ylmethoxy)-isoxazole-5-carboxylic acid (2,2,2-trifluoro-ethyl)-amide,
3-(5-Methyl-3-pyridin-2-yl-isoxazol-4-ylmethoxy)-isoxazole-5-carboxylic acid isopropyl-amide,
3-(5-Methyl-3-phenyl-isoxazol-4-ylmethoxy)-isoxazole-5-carboxylic acid morpholin-4-yl-amide,
3-(3-Butyl-5-methyl-isoxazol-4-ylmethoxy)-isoxazole-5-carboxylic acid (tetrahydro-furan-3(R)-yl)-amide
3-(5-Methyl-3-pyridin-2-yl-isoxazol-4-ylmethoxy)-isoxazole-5-carboxylic acid (2-hydroxy-ethyl)-amide,
3-[3-(5-Fluoro-pyridin-2-yl)-5-methyl-isoxazol-4-ylmethoxy]-isothiazole-5-carboxylic acid (tetrahydro-furan-3-yl)-amide,
3-(5-Methyl-3-phenyl-isoxazol-4-ylmethoxy)-isoxazole-5-carboxylic acid (tetrahydro-furan-3-yl)-amide,
3-(5-Methyl-3-pyridin-2-yl-isoxazol-4-ylmethoxy)-isoxazole-5-carboxylic acid piperidin-1-ylamide,
3-(3-Butyl-5-methyl-isoxazol-4-ylmethoxy)-isoxazole-5-carboxylic acid (tetrahydro-furan-3(S)-yl)-amide
3-(5-Methyl-3-phenyl-isoxazol-4-ylmethoxy)-isoxazole-5-carboxylic acid isopropylamide,
3-(5-Methyl-3-pyridin-2-yl-isoxazol-4-ylmethoxy)-isoxazole-5-carboxylic acid pyrrolidin-1-ylamide,
3-(5-Methyl-3-phenyl-isoxazol-4-ylmethoxy)-isoxazole-5-carboxylic acid (2-hydroxy-ethyl)-amide,
3-(3-Butyl-5-methyl-isoxazol-4-ylmethoxy)-isoxazole-5-carboxylic acid (tetrahydro-furan-3-yl)-amide,
3-(5-Methyl-3-phenyl-isoxazol-4-ylmethoxy)-isoxazole-5-carboxylic acid (2-hydroxy-1-methyl-ethyl)-amide, and
3-(5-Methyl-3-pyridin-2-yl-isoxazol-4-ylmethoxy)-isoxazole-5-carboxylic acid N',N'-dimethyl-hydrazide,
or pharmaceutically active salts or esters thereof.

One further embodiment of the invention provides compounds, selected from the group consisting of 3-[3-(5-Fluoro-pyridin-2-yl)-5-methyl-isoxazol-4-ylmethoxy]-isoxazole-5-carboxylic acid isopropylamide,
3-[3-(5-Fluoro-pyridin-2-yl)-5-methyl-isoxazol-4-ylmethoxy]-isoxazole-5-carboxylic acid (2-hydroxy-ethyl)-amide,
3-[3-(5-Fluoro-pyridin-2-yl)-5-methyl-isoxazol-4-ylmethoxy]-isothiazole-5-carboxylic acid isopropylamide,
3-[3-(5-Fluoro-pyridin-2-yl)-5-methyl-isoxazol-4-ylmethoxy]-isothiazole-5-carboxylic acid (2-hydroxy-ethyl)-amide, and
3-[3-(5-Fluoro-pyridin-2-yl)-5-methyl-isoxazol-4-ylmethoxy]-isothiazole-5-carboxylic acid (tetrahydro-furan-3-yl)-amide,
or pharmaceutically active salts or esters thereof.

One further embodiment of the invention provides compounds, selected from the group consisting of 3-(5-Methyl-3-phenyl-isoxazol-4-ylmethoxy)-isoxazole-5-carboxylic acid isopropylamide,
3-(5-Methyl-3-phenyl-isoxazol-4-ylmethoxy)-isoxazole-5-carboxylic acid (tetrahydro-furan-3-yl)-amide,
3-(5-Methyl-3-phenyl-isoxazol-4-ylmethoxy)-isoxazole-5-carboxylic acid (2-hydroxy-ethyl)-amide, 3-(5-Methyl-3-phenyl-isoxazol-4-ylmethoxy)-isoxazole-5-carboxylic acid (2-hydroxy-1-methyl-ethyl)-amide,
Acetic acid 2-{[3-(5-methyl-3-phenyl-isoxazol-4-yl-methoxy)-isoxazole-5-carbonyl]-amino}-ethyl ester,
3-(5-Methyl-3-phenyl-isoxazol-4-ylmethoxy)-isoxazole-5-carboxylic acid ((S)-2-hydroxy-1-methyl-ethyl)-amide,
3-(5-Methyl-3-phenyl-isoxazol-4-ylmethoxy)-isoxazole-5-carboxylic acid piperidin-1-ylamide,
3-(5-Methyl-3-phenyl-isoxazol-4-ylmethoxy)-isoxazole-5-carboxylic acid pyrrolidin-1-ylamide,
3-(5-Methyl-3-phenyl-isoxazol-4-ylmethoxy)-isoxazole-5-carboxylic acid morpholin-4-ylamide,
3-(5-Methyl-3-pyridin-2-yl-isoxazol-4-ylmethoxy)-isoxazole-5-carboxylic acid isopropyl amide,
3-(5-Methyl-3-pyridin-2-yl-isoxazol-4-ylmethoxy)-isoxazole-5-carboxylic acid (2-hydroxy-ethyl)-amide,
3-(5-Methyl-3-pyridin-2-yl-isoxazol-4-ylmethoxy)-isoxazole-5-carboxylic acid (tetrahydro-furan-3-yl)-amide,
3-(5-Methyl-3-pyridin-2-yl-isoxazol-4-ylmethoxy)-isoxazole-5-carboxylic acid (2,2,2-trifluoro-ethyl)-amide,
3-(5-Methyl-3-pyridin-2-yl-isoxazol-4-ylmethoxy)-isoxazole-5-carboxylic acid N',N'-dimethyl-hydrazide,
3-(5-Methyl-3-pyridin-2-yl-isoxazol-4-ylmethoxy)-isoxazole-5-carboxylic acid morpholin-4-ylamide,
3-(5-Methyl-3-pyridin-2-yl-isoxazol-4-ylmethoxy)-isoxazole-5-carboxylic acid piperidin-1-ylamide,
3-(5-Methyl-3-pyridin-2-yl-isoxazol-4-ylmethoxy)-isoxazole-5-carboxylic acid pyrrolidin-1-ylamide,
3-[3-(5-Fluoro-pyridin-2-yl)-5-methyl-isoxazol-4-yl-methoxy]-isoxazole-5-carboxylic acid isopropylamide,
3-[3-(5-Fluoro-pyridin-2-yl)-5-methyl-isoxazol-4-yl-methoxy]-isoxazole-5-carboxylic acid (2-hydroxy-ethyl)-amide,
3-(3-Butyl-5-methyl-isoxazol-4-ylmethoxy)-isoxazole-5-carboxylic acid (tetrahydro-furan-3-yl)-amide,
3-(3-Butyl-5-methyl-isoxazol-4-ylmethoxy)-isoxazole-5-carboxylic acid (tetrahydro-furan-3(R)-yl)-amide,
3-(3-Butyl-5-methyl-isoxazol-4-ylmethoxy)-isoxazole-5-carboxylic acid (tetrahydro-furan-3(S)-yl)-amide,
3-(3-Butyl-5-methyl-isoxazol-4-ylmethoxy)-isoxazole-5-carboxylic acid morpholin-4-ylamide,
3-(5-Methyl-3-pyridin-2-yl-isoxazol-4-ylmethoxy)-isothiazole-5-carboxylic acid isopropyl amide,
3-(5-Methyl-3-pyridin-2-yl-isoxazol-4-ylmethoxy)-isothiazole-5-carboxylic acid (2-hydroxy-ethyl)-amide,
3-[3-(5-Fluoro-pyridin-2-yl)-5-methyl-isoxazol-4-yl-methoxy]-isothiazole-5-carboxylic acid isopropylamide,
3-[3-(5-Fluoro-pyridin-2-yl)-5-methyl-isoxazol-4-yl-methoxy]-isothiazole-5-carboxylic acid (2-hydroxy-ethyl)-amide, and
3-[3-(5-Fluoro-pyridin-2-yl)-5-methyl-isoxazol-4-yl-methoxy]-isothiazole-5-carboxylic acid (tetrahydro-furan-3-yl)-amide,
or pharmaceutically active salts or esters thereof.

One further embodiment of the invention provides compounds, selected from the group consisting of 3-(5-Methyl-3-pyridin-2-yl-isoxazol-4-ylmethoxy)-isoxazole-5-carboxylic acid (tetrahydro-furan-3-yl)-amide,
3-[3-(5-Fluoro-pyridin-2-yl)-5-methyl-isoxazol-4-yl-methoxy]-isoxazole-5-carboxylic acid isopropylamide,
3-(5-Methyl-3-pyridin-2-yl-isoxazol-4-ylmethoxy)-isoxazole-5-carboxylic acid morpholin-4-ylamide,
3-[3-(5-Fluoro-pyridin-2-yl)-5-methyl-isoxazol-4-yl-methoxy]-isoxazole-5-carboxylic acid (2-hydroxy-ethyl)-amide,
3-(5-Methyl-3-pyridin-2-yl-isoxazol-4-ylmethoxy)-isoxazole-5-carboxylic acid (2,2,2-trifluoro-ethyl)-amide,
3-(5-Methyl-3-pyridin-2-yl-isoxazol-4-ylmethoxy)-isoxazole-5-carboxylic acid isopropyl amide,
3-(5-Methyl-3-phenyl-isoxazol-4-ylmethoxy)-isoxazole-5-carboxylic acid morpholin-4-ylamide,
3-(3-Butyl-5-methyl-isoxazol-4-ylmethoxy)-isoxazole-5-carboxylic acid (tetrahydro-furan-3(S)-yl)-amide
3-(5-Methyl-3-pyridin-2-yl-isoxazol-4-ylmethoxy)-isoxazole-5-carboxylic acid (2-hydroxy-ethyl)-amide,
3-[3-(5-Fluoro-pyridin-2-yl)-5-methyl-isoxazol-4-yl-methoxy]-isothiazole-5-carboxylic acid (tetrahydro-furan-3-yl)-amide,
3-(5-Methyl-3-phenyl-isoxazol-4-ylmethoxy)-isoxazole-5-carboxylic acid (tetrahydro-furan-3-yl)-amide,
3-(5-Methyl-3-pyridin-2-yl-isoxazol-4-ylmethoxy)-isoxazole-5-carboxylic acid piperidin-1-ylamide, and
3-(3-Butyl-5-methyl-isoxazol-4-ylmethoxy)-isoxazole-5-carboxylic acid (tetrahydro-furan-3(R)-yl)-amide,
or pharmaceutically active salts or esters thereof.

One further embodiment of the invention is a process for preparing a compound as defined in any embodiment, which process comprises reacting a compound formula XII with a compound of formula XV

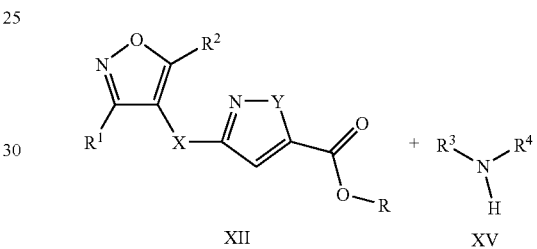

wherein
R is lower alkyl, and $R^1$, $R^2$, $R^3$, $R^4$, X and Y are as defined in any of the embodiments. One further embodiment of the invention is a compound according to any embodiment, whenever prepared by a process as defined above.

One further embodiment of the invention is a compound according to any embodiment for use as a medicament.

One further embodiment of the invention is a compound according to any embodiment for the use for the therapeutic and/or prophylactic treatment of a disorder or condition mediated by the GABA A α5 receptor, or that can be treated via modulation of the GABA A α5 receptor.

One further embodiment of the invention is a compound according to any embodiment for the use for the therapeutic and/or prophylactic treatment of chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers.

One further embodiment of the invention is a medicament, comprising a compound according to any embodiment.

One further embodiment of the invention is a pharmaceutical composition comprising a compound according to any embodiment as an active ingredient and a pharmaceutically acceptable carrier and/or a pharmaceutically acceptable auxiliary substance.

One further embodiment of the invention is a pharmaceutical composition, comprising a compound according to any embodiment for the therapeutic and/or prophylactic treatment of a disorder or condition mediated by the GABA A α5 receptor, or that can be treated via modulation of the GABA A α5 receptor.

One further embodiment of the invention is a pharmaceutical composition, comprising a compound according to any embodiment for the therapeutic and/or prophylactic treatment of chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers.

One further embodiment of the invention is the use of a compound according to any embodiment for the manufacture of a medicament for the therapeutic and/or prophylactic treatment of a disorder or condition mediated by the GABA A α5 receptor, or that can be treated via modulation of the GABA A α5 receptor.

One further embodiment of the invention is the use of a compound according to any embodiment for the manufacture of a medicament for the therapeutic and/or prophylactic treatment of chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers.

One further embodiment of the invention is the use of a compound according to any embodiment for the therapeutic and/or prophylactic treatment of a disorder or condition mediated by the GABA A α5 receptor, or that can be treated via modulation of the GABA A α5 receptor.

One further embodiment of the invention is the use of a compound according to any embodiment for the therapeutic and/or prophylactic treatment of chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers.

One further embodiment of the invention is a method for the therapeutic and/or prophylactic treatment of a disorder or condition mediated by the GABA A α5 receptor, or that can be treated via modulation of the GABA A α5 receptor, particularly for the therapeutic and/or prophylactic treatment of chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers, which method comprises administering a compound according to any embodiment to a mammal, particularly to a human being.

The compounds of formula I can be prepared in accordance with the following schemes. The starting material is commercially available or can be prepared in accordance with known methods. Any previously defined residues and variables will continue to have the previously defined meaning unless otherwise indicated.

a) reacting a compound of formula III

with hydroxylamine hydrochloride in a suitable solvent, such as ethanol and water, in the presence of a base, such as aqueous sodium hydroxide, to give a compound of formula IV:

b) reacting the compound of formula IV with a chlorinating agent, such as N-chlorosuccinimide, in a suitable solvent, such as DMF, to give a compound of formula V:

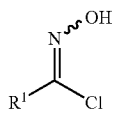

c) and then reacting the compound of formula V with a compound of formula VI:

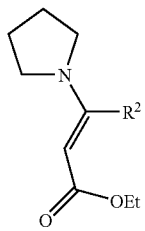

to give a compound of formula VII:

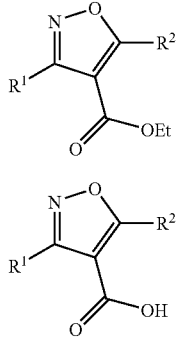

d) reacting a compound of formula VII with a reducing agent, such as lithiumaluminiumhydride, in a suitable solvent, such as THF, to give a compound of formula XV or reacting a compound of formula VII with a hydrolytic agent, such as NaOH or LiOH, in a suitable solvent, such as THF, MeOH or EtOH, and water to give a compound of formula VIII, followed by reacting a compound of formula VIII with a reducing agent, such as lithiumaluminiumhydride or ethylchloroformate, in the presence of sodiumborohydride in a suitable solvent, such as THF or water, to give a compound of formula IX;

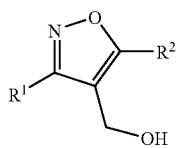

e) reacting a compound of formula IX with an oxidizing agent, such as manganese dioxide or PCC, in a suitable solvent, such as dichloromethane, to give a compound of formula X:

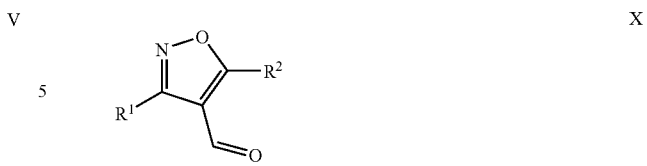

f) reacting a compound of formula XI with a compound of formula

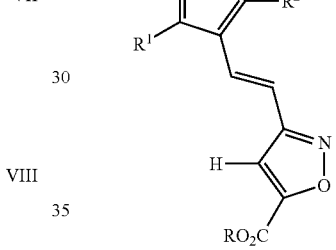

to give a compound of formula XIIa

g) followed by reacting a compound of formula XIIa to compounds of formula I via standard methods.

In a further embodiment, the present compounds of formula I and their pharmaceutically acceptable salts and esters can be prepared by a process comprising the steps of:

a) reacting a compound of formula IX

b) with a compound of formula XIII or XIV under Mitsunobu reaction conditions with an appropriate alcohol -continued

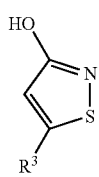

XIV c) to give a compound of formulas XIIb or XIIc respectively and converting to compounds of formula I via standard methods.

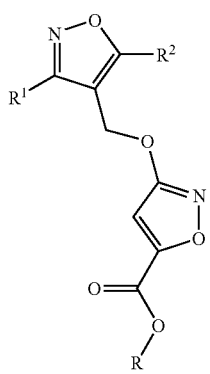

XIIb

-continued

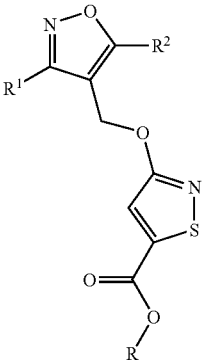

XIIc

Compounds of formula XVI can react with a compound such as XVVVII in the presence of triphenylphosphine and diethyl azodicarboxylate (or diispropyl azodicarboxylate), in a suitable solvent, such as THF, to give a compound of formula XVIII, followed by reacting with an oxidizing agent, such as Osmium(VIII)-oxide, in the presence of NMO to give a bishydroxylated compound of formula XX. XX can be oxidized with e.g. sodium metaperiodate to the corresponding aldehyde XIX, which can be further treated with a reducing agent, such as lithium borohydride, to give a compound of formula XIId.

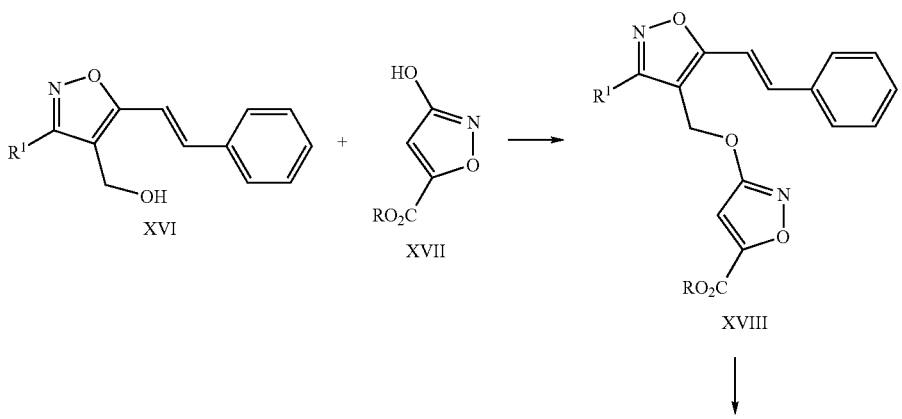

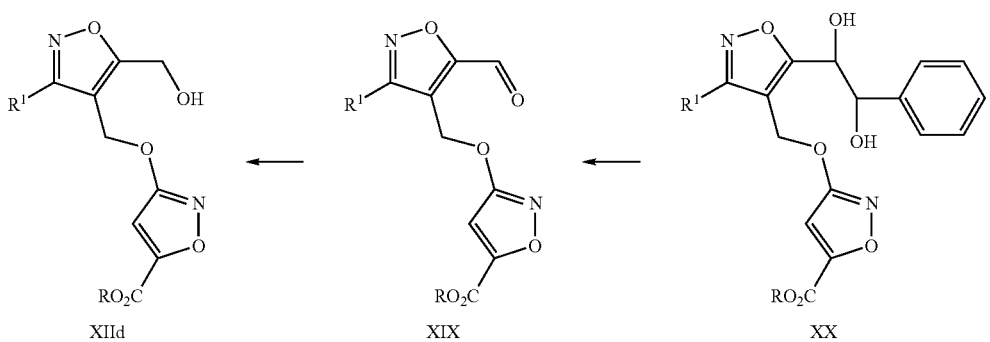

In accordance with Scheme 1, compounds of formula I can be prepared following standard methods from compounds of formula XII, i.e. XIIa, XIIb, XIIc and XIId.

Scheme 1: Preparation of compounds of formula I

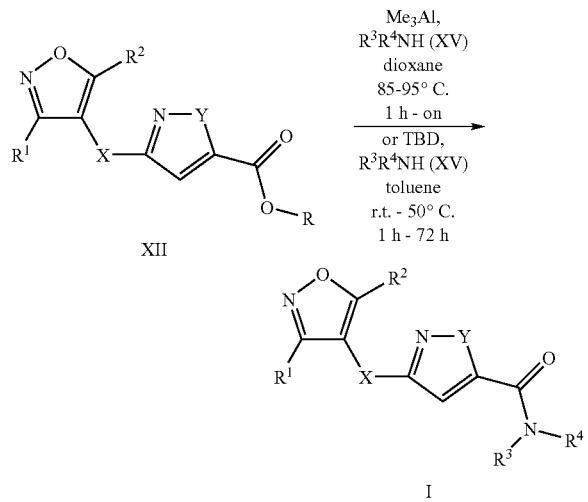

Pharmacological Tests

The compounds of formula I and their pharmaceutically acceptable salts and esters possess valuable pharmacological properties. Compounds of the present invention are ligands for GABA A receptors containing the α5 subunit and are therefore useful in therapy where cognition enhancement is required.

The compounds were investigated in accordance with the test given hereinafter:

Membrane Preparation and Binding Assay

The affinity of compounds at GABA A receptor subtypes was measured by competition for [3H]flumazenil (85 Ci/mmol; Roche) binding to HEK293 cells expressing rat (stably transfected) or human (transiently transfected) receptors of composition α1β3γ2, α2β3γ2, α3β3γ2 and α5β3γ2.

Cell pellets were suspended in Krebs-tris buffer (4.8 mM KCl, 1.2 mM $CaCl_2$, 1.2 mM $MgCl_2$, 120 mM NaCl, 15 mM Tris; pH 7.5; binding assay buffer), homogenized by polytron for ca. 20 sec on ice and centrifuged for 60 min at 4° C. (50000 g; Sorvall, rotor: SM24=20000 rpm). The cell pellets were re-suspended in Krebs-tris buffer and homogenized by polytron for ca. 15 sec on ice. Protein was measured (Bradford method, Bio-Rad) and aliquots of 1 mL were prepared and stored at −80° C.

Radioligand binding assays were carried out in a volume of 200 mL (96-well plates) which contained 100 mL of cell membranes, [$^3$H]flumazenil at a concentration of 1 nM for α1, α2 and α3 subunits and 0.5 nM for α5 subunits and the test compound in the range of $10\text{-}10^{-3} \times 10^{-6}$ M. Nonspecific binding was defined by $10^{-5}$ M diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity was detected by liquid scintillation counting. Ki values were calculated using Excel-Fit (Microsoft) and are the means of two determinations.

The compounds of the accompanying examples were tested in the above described assay, and the preferred compounds were found to possess a Ki value for displacement of [$^3$H]flumazenil from α5 subunits of the rat GABA A receptor of 100 nM or less. Most preferred are compounds with a Ki (nM)<35. In a preferred embodiment the compounds of the invention are binding selective for the α5 subunit relative to the α1, α2 and α3 subunit. Representative test results are listed below.

TABLE 2 human Ki (hKi) values

| Example | hKi GABA A α5 (nM) |
|---|---|
| 1 | 28.6 |
| 3 | 7.5 |
| 4 | 4.4 |
| 5 | 8 |
| 6 | 8.8 |
| 7 | 16.8 |
| 8 | 13.5 |
| 9 | 23.1 |
| 10 | 22.2 |
| 11 | 13.8 |
| 12 | 18.5 |
| 13 | 2.8 |
| 14 | 2.5 |
| 15 | 3 |
| 16 | 1.4 |
| 17 | 2.3 |
| 18 | 8.9 |
| 19 | 2 |
| 20 | 6 |
| 21 | 7.8 |
| 22 | 1.7 |
| 23 | 2.2 |
| 24 | 22.2 |
| 25 | 27.7 |
| 26 | 22.7 |
| 27 | 38 |
| 28 | 24.6 |
| 29 | 8.5 |
| 30 | 6.5 |
| 31 | 2.8 |
| 32 | 56.8 |
| 33 | 10.4 |
| 34 | 28 |
| 35 | 35 |
| 36 | 15 |
| 37 | 17.6 |
| 38 | 11.8 |
| 39 | 13 |
| 40 | 3.8 |
| 41 | 28.9 |
| 42 | 9.8 |
| 43 | 8.8 |
| 44 | 2.8 |
| 45 | 10.0 |

Pharmaceutical Preparations

The present invention also provides pharmaceutical compositions containing compounds of formula I as well as their pharmaceutically acceptable salts and esters and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The compounds of formula I and their pharmaceutically acceptable salts and esters can be processed with pharmaceutically inert, inorganic or organic excipients for the production of tablets, coated tablets, dragées and hard gelatin capsules. Examples of such excipients that are suitable for tablets, dragées and hard gelatin capsules are lactose, corn starch or derivatives thereof, talc, stearic acid or its salts etc. Suitable excipients for soft gelatin capsules are e.g. vegetable oils, waxes, fats, semisolid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

The pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt or ester thereof. The daily dosage can be administered as single dose or in divided doses and, in addition, the upper limit can also be exceeded when this is found to be indicated.

Pharmaceutical compositions of the invention can be formulated for any route of administration, such as oral, sublingual, buccal, parenteral (subcutaneous, intramuscular, intravenous), rectal, topical, intranasal and trough inhalation or insufflation, and comprise at least one compound of formula I or pharmaceutically active salts or esters thereof, with any pharmaceutically suitable ingredient, excipient, carrier, adjuvant or vehicle.

Examples of compositions according to the invention are, but are not limited to:

Example A

Tablets of the following composition are manufactured in the usual manner:

TABLE 3

| possible tablet composition | |
| --- | --- |
| ingredient | mg/tablet |
| Active substance | 5 |
| Lactose | 45 |
| Corn starch | 15 |
| Microcrystalline cellulose | 34 |
| Magnesium stearate | 1 |
| Tablet weight | 100 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Example B

Capsules of the following composition are manufactured:

TABLE 4

| possible capsule composition | |
| --- | --- |
| ingredient | mg/capsule |
| Active substance | 10 |
| Lactose | 155 |
| Corn starch | 30 |
| Talc | 5 |
| Capsule fill weight | 200 |

Manufacturing Procedure

1. Mix items 1, 2 and 3 in a suitable mixer for 30 minutes.
2. Add item 4 and mix for 3 minutes.
3. Fill into a suitable capsule.

The active substance, lactose and corn starch are firstly mixed in a mixer and then in a comminuting machine. The mixture is returned to the mixer, the talc is added thereto and mixed thoroughly. The mixture is filled by machine into hard gelatine capsules.

Example C

Suppositories of the following composition are manufactured:

TABLE 5

| possible suppository composition | |
| --- | --- |
| ingredient | mg/supp. |
| Active substance | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

Experimental Part

The following examples are provided for illustration of the invention. They should not be considered as limiting the scope of the invention, but merely as being representative thereof.

Intermediate 1

5-Methyl-4-(5-methyl-isoxazol-3-yloxymethyl)-3-phenyl-isoxazole

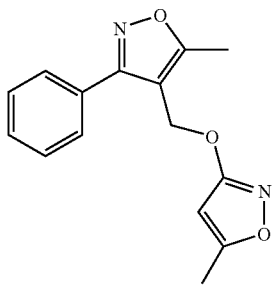

To a solution of (5-methyl-3-phenyl-isoxazol-4-yl)-methanol (378 mg, 2.0 mmol) in THF (7 mL) was added 3-hydroxy-5-methylisoxazole (200 mg, 2.0 mmol) and triphenylphosphine (629 mg, 2.0 mmol) at room temperature under an argon atmosphere. Then diethyl azodicarboxylate (~40% in toluene, 1.1 mL, 2.5 mmol) was added and the reaction mixture was stirred for 3 h at room temperature. Concentration and purification by chromatography (silica, heptane:ethyl acetate=6:4 to 0:1) afforded the title compound (214 mg, 40%) as a colourless oil. MS: m/e=271.0 [M+H]$^+$.

Example 1

3-[(E)-2-(3-Butyl-5-methyl-isoxazol-4-yl)-vinyl]-isoxazole-5-carboxylic acid (2-hydroxy-ethyl)-amide

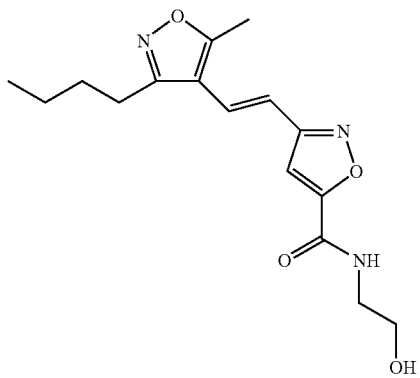

a) 3-Butyl-5-methyl-isoxazole-4-carboxylic acid ethyl ester

To a suspension of N-chlorosuccinimide (16.1 g, 121 mmol) in chloroform (250 mL) at room temperature was added pyridine (0.95 g, 12.0 mmol) then a solution of pentanal oxime (12.2 g, 121 mmol) in chloroform (250 mL) was added dropwise over 20 min. The reaction mixture was stirred at 50° C. for 2 h then cooled to room temperature and a solution of ethyl (E)-3-(1-pyrrolidino)-2-butenoate (22.1 g, 121 mmol) in chloroform (120 mL) added dropwise. The reaction mixture was warmed to 50° C. and a solution of triethylamine (12.2 g, 121 mmol) in chloroform (120 mL) added dropwise. After 15 h the reaction mixture was cooled and extracted with water then citric acid (10% w/w aqueous solution). The combined aqueous phases were extracted with dichloromethane, then the combined organic phases were dried, filtered and concentrated. Purification by chromatography (silica, heptane:ethyl acetate=100:0 to 9:1) afforded the title compound (10.9 g, 43%) as a pale yellow liquid. MS: m/e=232.2 [M+H]$^+$.

b) (3-Butyl-5-methyl-isoxazol-4-yl)-methanol

To a stirred solution of 3-butyl-5-methyl-isoxazole-4-carboxylic acid ethyl ester (9.8 g, 46.3 mmol) in THF (100 mL) under argon and at 0° C. was added lithium aluminium hydride (2.03 g, 53.4 mmol) in five portions. After 1 h the reaction mixture was quenched dropwise with Seignette's salt solution. The reaction mixture was filtered and the filtrate extracted with ethyl acetate. The combined organic extracts were washed with Seignette's salt solution then dried, filtered and concentrated. Purification by chromatography (silica, heptane:ethyl acetate=100:0 to 4:6) afforded the title compound (7.5 g, 95%) as a yellow liquid. MS: m/e=170.3 [M+H]$^+$.

c) 3-Butyl-5-methyl-isoxazole-4-carbaldehyde

To a stirred solution of PCC (4.96 g, 23 mmol) and anhydrous magnesium sulfate (7.40 g, 61 mmol) in DCM (60 mL) was added a solution of (3-butyl-5-methyl-isoxazol-4-yl)-methanol (2.6 g, 15 mmol) in DCM (60 mL) at room temperature and under argon. After 3 h the reaction mixture was diluted with ether (100 mL) and filtered through a bed of silica and the filtrate was concentrated. Purification by chromatography (silica heptane:ethyl acetate=100:0 to 1:1) afforded the title compound (2.15 g, 84%) as a colourless liquid. MS: m/e=170.3 [M+H]$^+$.

d) (Diphenyl-phosphinoyl)-acetaldehyde

To a solution of methyldiphenylphosphine oxide (2.0 g, 9.0 mmol) in THF (60 mL) at 0° C. was added BuLi (1.6 M in hexane, 6.94 mL, 11.0 mmol) and after 2 h at 0° C., the mixture was cooled to −78° C. and then DMF (0.85 mL, 11 mmol) was added. After 2 h at −78° C. the mixture was quenched with HCl (1 N, 25 mL) and the resulting mixture warmed up to room temperature. The mixture was extracted with ethyl acetate and the combined organic layers were then washed with water and brine and then dried over sodium sulfate, filtered and evaporated. The crude product (off-white oil, 2.41 g) was used directly in the next step. MS: m/e=245.2 [M+H]$^+$.

e) (E)- and/or (Z)-(diphenyl-phosphinoyl)-acetaldehyde oxime

To a suspension of (diphenyl-phosphinoyl)-acetaldehyde example 1d (2.4 g, 9.0 mmol) and hydroxylamine hydrochloride (0.68 g, 10.0 mmol) in ethanol (50 mL) and water (100 mL) was added at 0° C. an aqueous solution of sodium hydroxide (50%, 5 mL) added dropwise within a 10 min period. After stirring at room temperature overnight, the resulting mixture was acidified with HCl (4 N). The mixture was then extracted with dichloromethane and the combined organic layers were then washed with water and brine and then dried over sodium sulfate, filtered and evaporated to afford the title compound (3.75 g, 98%) which was obtained as a light yellow solid. MS m/e (EI): 260.0 [M].

f) 3-(Diphenyl-phosphinoylmethyl)-isoxazole-5-carboxylic acid ethyl ester

A solution of (E)- and/or (Z)-(diphenyl-phosphinoyl)-acetaldehyde oxime if (3.7 g, 9.0 mmol) in chloroform (7 mL) containing pyridine (3 drops) was added in one portion to a suspension of N-chlorosuccinimide (1.14 g, 9.0 mmol) in chloroform (7 mL) and the resulting mixture stirred at room temperature for 3 h and then heated at 50° C. for 1.5 h. The mixture was then cooled to room temperature and ethyl propiolate (1.05 mL, 10.0 mmol) added after 15 min triethylamine (1.42 mL, 10.0 mmol) was added dropwise. The resulting mixture was then stirred overnight and then extracted with dichloromethane and the combined organic layers were then washed with water and brine and then dried over sodium sulfate, filtered and evaporated to afford the title compound (420 mg, 14%) which was obtained as an off white solid. MS: m/e=356.1 [M+H]$^+$.

g) 3-[(E)-2-(3-Butyl-5-methyl-isoxazol-4-yl)-vinyl]-isoxazole-5-carboxylic acid ethyl ester To a solution of 3-(diphenyl-phosphinoylmethyl)-isoxazole-5-carboxylic acid ethyl ester (410 mg, 1.2 mmol) in THF (10 mL) at −78° C. was added BuLi (1.6 M in hexanes, 0.79 mL, 1.3 mmol) and the mixture warmed up to 0° C. over 1 h and a solution of 3-butyl-5-methyl-isoxazole-4-carbaldehyde (193 mg, 1.2 mmol) in THF (5 mL) added and stirred for 2 h. The mixture was extracted with ethyl acetate and the combined organic layers were then washed with water and brine and then dried over sodium sulfate, filtered and evaporated. Purification by chromatography (silica, heptane:ethyl acetate=100:0 to 7:3) afforded the title compound (75 mg, 21%) as a colourless oil. MS: m/e=305.2 [M+H]$^+$.

h) 3-[(E)-2-(3-Butyl-5-methyl-isoxazol-4-yl)-vinyl]-isoxazole-5-carboxylic acid (2-hydroxy-ethyl)-amide To a solution of 3-[(E)-2-(3-butyl-5-methyl-isoxazol-4-yl)-vinyl]-isoxazole-5-carboxylic acid ethyl ester (70 mg, 0.23 mmol) and ethanolamine (28 mg, 0.46 mmol) in toluene (1 mL) was added 1,5,7-triazabicyclo[4.4.0]dec-5-ene (10 mg, 0.07 mmol) and the reaction stirred under argon overnight at room temperature. Then silica (1 g) was added and the mixture evaporated and the residue purified by chromatography (silica, dichloromethane:methanol=9:1 to 7:3) to afford the title compound (20 mg, 27%) which was obtained as a white solid. MS: m/e=320.1 [M+H]$^+$.

Example 3

3-(5-Methyl-3-phenyl-isoxazol-4-ylmethoxy)-isoxazole-5-carboxylic acid isopropylamide

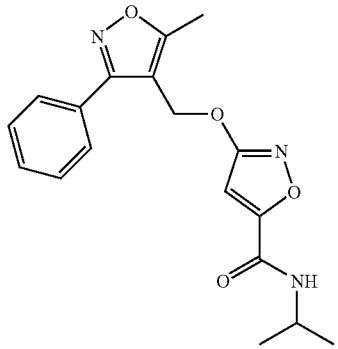

a) 3-Oxo-2,3-dihydro-isoxazole-5-carboxylic acid methyl ester

Prepared according to *Synthesis* 1985, 1100. To a stirred solution of N-hydroxyurea (3.80 g, 50 mmol) and 1,5-diazabicyclo[5.4.0]undec-5-ene (8.37 g, 55 mmol) in methanol (50 mL) with cooling (ice bath) was added dimethyl ethyne dicarboxylate (7.11 g, 50 mmol) dropwise over 20 min. A dark red colour appeared then dissipated with each drop added, until finally a deep orange/red clear solution had formed. After an additional 20 min the mixture was concentrated to give a red oil which was then acidified with cooling in an ice/water bath to pH 1 with HCl (conc.). The resulting yellow mixture was extracted with diethyl ether (3×40 mL) then the aqueous phase was saturated with brine and extracted with ether (2×50 mL). The combined organic layers were then washed with water and brine and then dried over sodium sulfate, filtered and evaporated to afford the title compound (2.89 g, 40%) as white crystals after recrystallisation from chloroform. MS: m/e=143.8 [M+H]$^+$.

b) 3-(5-Methyl-3-phenyl-isoxazol-4-ylmethoxy)-isoxazole-5-carboxylic acid methyl ester As described for Intermediate 1, (5-methyl-3-phenyl-isoxazol-4-yl)-methanol (1.0 g, 5.3 mmol) was converted, using 3-oxo-2,3-dihydro-isoxazole-5-carboxylic acid methyl ester (756 mg, 5.3 mmol) instead of 3-hydroxy-5-methylisoxazole, to the title compound (1.04 g, 63%) which was obtained as a colourless gum after purification by chromatography (silica, heptane:ethyl acetate=4:1 to 0:1). MS: m/e=315.0 [M+H]$^+$.

c) 3-(5-Methyl-3-phenyl-isoxazol-4-ylmethoxy)-isoxazole-5-carboxylic acid isopropylamide A solution of trimethylaluminium (2 M in toluene, 1.27 mL, 2.6 mmol) was added dropwise (exothermic) to a solution of isopropyl amine (220 µL, 2.6 mmol) in dioxane (6 mL) and the resulting mixture was stirred at room temperature for 30 min. Then 3-(5-methyl-3-phenyl-isoxazol-4-ylmethoxy)-isoxazole-5-carboxylic acid methyl ester (230 mg, 0.73 mmol) was added. The resulting mixture was then heated at 85-90° C. for 30 min and then cooled to room temperature and then poured into Seignette's salt and extracted with ethyl acetate which was then washed with brine, dried over sodium sulfate and evaporated. Purification by chromatography (silica, heptane:ethyl acetate=4:1 to 0:1) afforded the title compound (184 mg, 74%) which was obtained as a white solid. MS: m/e=342.1 [M+H]$^+$.

Example 4

3-(5-Methyl-3-phenyl-isoxazol-4-ylmethoxy)-isoxazole-5-carboxylic acid (tetrahydro-furan-3-yl)-amide

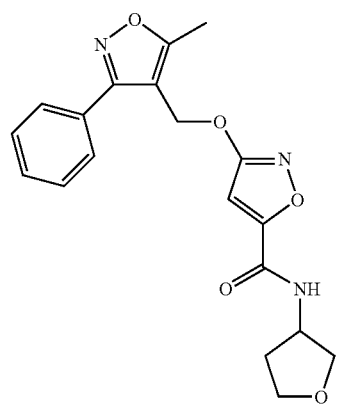

To a solution of 3-(5-methyl-3-phenyl-isoxazol-4-yl-methoxy)-isoxazole-5-carboxylic acid methyl ester (298 mg, 0.95 mmol) and tetrahydrofuran-3-ylamine (99 mg, 1.14 mmol) in toluene (1.5 mL) was added 1,5,7-triazabicyclo[4.4.0]dec-5-ene (40 mg, 0.28 mmol) and the reaction stirred under argon overnight at 50° C. Then the mixture was evaporated and the residue purified by chromatography (silica, heptane:ethyl acetate=4:1 to 1:1) to afford the title compound (87 mg, 25%) which was obtained as a colourless gum. MS: m/e=370.1 [M+H]$^+$.

Example 5

3-(5-Methyl-3-phenyl-isoxazol-4-ylmethoxy)-isoxazole-5-carboxylic acid (2-hydroxy-ethyl)-amide

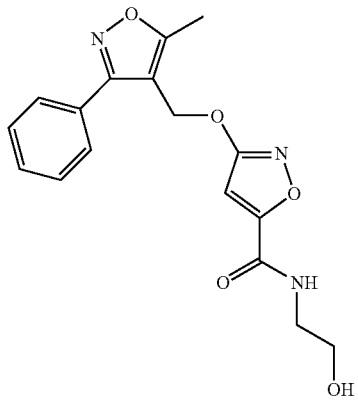

As described for example 4,3-(5-methyl-3-phenyl-isoxazol-4-ylmethoxy)-isoxazole-5-carboxylic acid methyl ester (242 mg, 0.77 mmol) was converted, using 2-hydroxyethylamine (56 mg, 0.92 mmol) instead of tetrahydrofuran-3-ylamine, to the title compound (86 mg, 33%) which was obtained as a white solid after purification by chromatography (silica, heptane:ethyl acetate=7:3 to 0:1). MS: m/e=344.1 [M+H]$^+$.

Example 6

3-(5-Methyl-3-phenyl-isoxazol-4-ylmethoxy)-isoxazole-5-carboxylic acid (2-hydroxy-1-methyl-ethyl)-amide

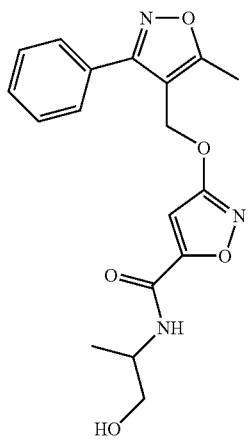

As described for example 4,3-(5-methyl-3-phenyl-isoxazol-4-ylmethoxy)-isoxazole-5-carboxylic acid methyl ester (263 mg, 0.84 mmol) was converted, using 1-hydroxymethylethylamine (75 mg, 1.0 mmol) instead of tetrahydrofuran-3-ylamine, to the title compound (192 mg, 64%) which was obtained as a white solid after purification by chromatography (silica, heptane:ethyl acetate=7:3 to 0:1). MS: m/e=358.1 [M+H]$^+$.

Example 7

Acetic acid 2-{[3-(5-methyl-3-phenyl-isoxazol-4-ylmethoxy)-isoxazole-5-carbonyl]-amino}-ethyl ester

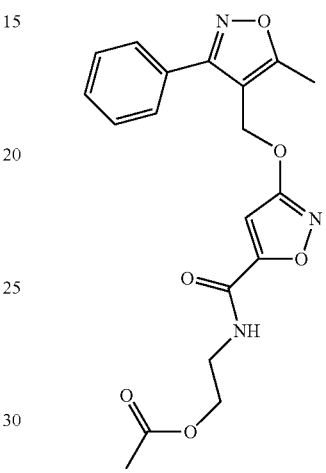

As described for example 4,3-(5-methyl-3-phenyl-isoxazol-4-ylmethoxy)-isoxazole-5-carboxylic acid methyl ester (242 mg, 0.77 mmol) was converted, using 2-hydroxyethylamine (56 mg, 0.92 mmol) instead of tetrahydrofuran-3-ylamine, to the title compound (77 mg, 26%) which was obtained as a colourless gum after purification by chromatography (silica, heptane:ethyl acetate=7:3 to 0:1). MS: m/e=386.0 [M+H]$^+$.

Example 8

(R or S)-3-(5-Methyl-3-phenyl-isoxazol-4-ylmethoxy)-isoxazole-5-carboxylic acid (2-hydroxy-1-methyl-ethyl)-amide

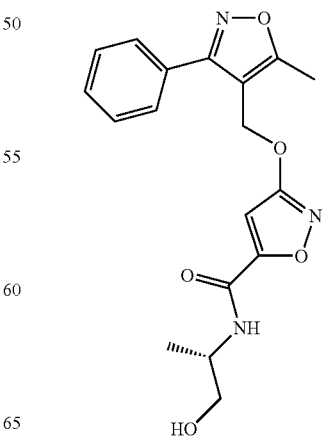

The stereoisomers of 3-(5-methyl-3-phenyl-isoxazol-4-yl-methoxy)-isoxazole-5-carboxylic acid (2-hydroxy-1-methyl-ethyl)-amide (example 6, 98 mg) in ethanol:heptane (1:2, 6 mL) were separated using a 5×50 cm Chiralpak AD column at room temperature using an isopropanol:heptane (2:8) mobile phase with UV detection at 220 nM. The least polar component (−ve sign of rotation) was obtained as a white solid (35 mg). MS: m/e=358.2 [M+H]$^+$.

Example 9

(S or R)-3-(5-Methyl-3-phenyl-isoxazol-4-yl-methoxy)-isoxazole-5-carboxylic acid (2-hydroxy-1-methyl-ethyl)-amide

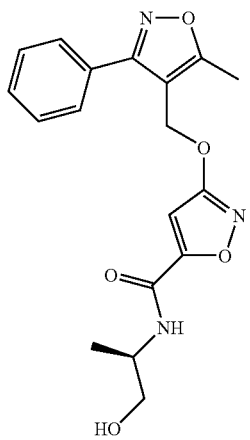

The stereoisomers of 3-(5-methyl-3-phenyl-isoxazol-4-yl-methoxy)-isoxazole-5-carboxylic acid (2-hydroxy-1-methyl-ethyl)-amide (example 6, 98 mg) in ethanol:heptane (1:2, 6 mL) were separated using a 5×50 cm Chiralpak AD column at room temperature using an isopropanol:heptane (2:8) mobile phase with UV detection at 220 nM. The least polar component (+ve sign of rotation) was obtained as a white solid (35 mg). MS: m/e=358.2 [M+H]$^+$.

Example 10

3-(5-Methyl-3-phenyl-isoxazol-4-ylmethoxy)-isoxazole-5-carboxylic acid N',N'-dimethyl-hydrazide

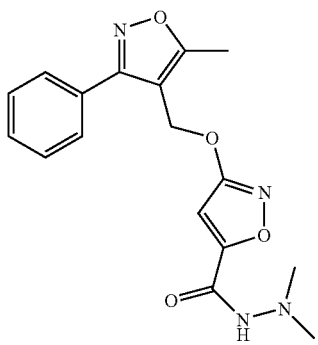

A solution of trimethylaluminium (2 M in toluene, 0.6 mL, 1.3 mmol) was added dropwise (exothermic) to a solution of N,N-dimethylhydrazine (76 mg, 1.3 mmol) in dioxane (5 mL) and the resulting mixture was stirred at room temperature for 1 h. Then 3-(5-methyl-3-phenyl-isoxazol-4-ylmethoxy)-isoxazole-5-carboxylic acid methyl ester (100 mg, 0.32 mmol) was added. The resulting mixture was then heated at 85-90° C. for 4 h and then cooled to room temperature and then poured into Seignette's salt and extracted with ethyl acetate which was then washed with brine, dried over sodium sulfate and evaporated. Purification by chromatography (silica, dichloromethane:methanol=9:1 to 4:1) afforded the title compound (24 mg, 22%) which was obtained as a colourless oil. MS: m/e=343.3 [M+H]$^+$.

Example 11

3-(5-Methyl-3-phenyl-isoxazol-4-ylmethoxy)-isoxazole-5-carboxylic acid piperidin-1-yl-amide

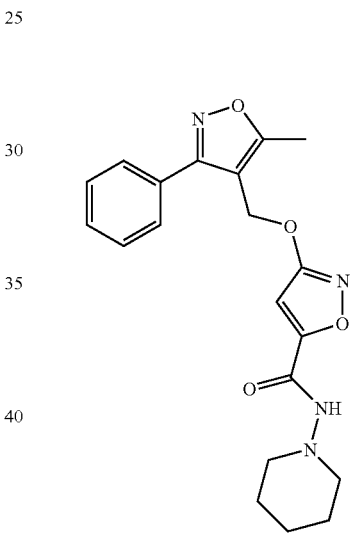

A solution of trimethylaluminium (2 M in toluene, 0.6 mL, 1.3 mmol) was added dropwise (exothermic) to a solution of 1-aminopiperidine (127 mg, 1.3 mmol) in dioxane (3 mL) and the resulting mixture was stirred at room temperature for 1 h. Then a solution of 3-(5-methyl-3-phenyl-isoxazol-4-ylmethoxy)-isoxazole-5-carboxylic acid methyl ester (100 mg, 0.32 mmol) in dioxane (2 mL) was added. The resulting mixture was then heated at 85-90° C. for 4 h and then cooled to room temperature, stirred overnight, and then poured into Seignette's salt and extracted with ethyl acetate which was then washed with brine, dried over sodium sulfate and evaporated. Purification by chromatography (silica, dichloromethane:methanol=9:1 to 4:1) afforded the title compound (100 mg, 82%) which was obtained as a white solid. MS: m/e=383.3 [M+H]$^+$.

Example 12

3-(5-Methyl-3-phenyl-isoxazol-4-ylmethoxy)-isoxazole-5-carboxylic acid pyrrolidin-1-yl-amide

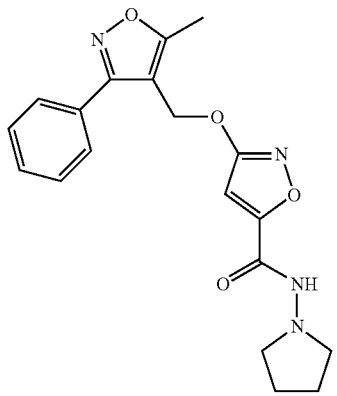

a) 3-(5-Methyl-3-phenyl-isoxazol-4-ylmethoxy)-isoxazole-5-carboxylic acid

To a solution of 3-(5-methyl-3-phenyl-isoxazol-4-ylmethoxy)-isoxazole-5-carboxylic acid methyl ester (209 mg, 0.66 mmol) in dioxane (5 mL) was added aqueous sodium hydroxide (2 N, 2 mL). After heating at reflux for 1 h the mixture was cooled to room temperature and acidified with HCl (4 N, 2 mL). Purification by filtration and drying afforded the title compound (187 mg, 94%) which was obtained as a white solid. MS: m/e=299.1 [M−H]$^-$.

b) 3-(5-Methyl-3-phenyl-isoxazol-4-ylmethoxy)-isoxazole-5-carboxylic acid pyrrolidin-1-yl-amide To a solution of 3-(5-methyl-3-phenyl-isoxazol-4-ylmethoxy)-isoxazole-5-carboxylic acid (120 mg, 0.4 mmol) in DMF (5 mL) were added 2-(1H-benzotriazole-1-yl)-1,1,3,3-tetramethyluronium tetrafluoroborate (192 mg, 0.6 mmol), N,N-diisopropyl ethyl amine (340 µL, 2.0 mmol) and N-aminopyrrolidine HCl (64 mg, 0.52 mmol). The resulting reaction mixture was for 4 h at room temperature. Concentration and purification by chromatography (silica, dichloromethane:methanol=1:0 to 4:1) afforded the title compound (108 mg, 73%) as a colourless oil. MS: m/e=369.2 [M+H]$^+$.

Example 13

3-(5-Methyl-3-phenyl-isoxazol-4-ylmethoxy)-isoxazole-5-carboxylic acid morpholin-4-ylamide

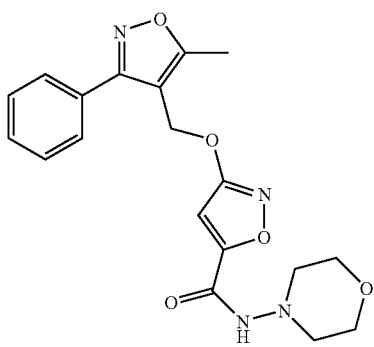

As described for example 12b, 3-(5-methyl-3-phenyl-isoxazol-4-ylmethoxy)-isoxazole-5-carboxylic acid (65 mg, 0.22 mmol) was converted, using 4-amino-morpholine (29 mg, 0.28 mmol) instead of N-aminopyrrolidine HCl, to the title compound (58 mg, 70%) which was obtained as a white solid after purification by chromatography (silica, dichloromethane:methanol=1:0 to 9:1). MS: m/e=385.2 [M+H]$^+$.

Example 14

3-(5-Methyl-3-pyridin-2-yl-isoxazol-4-ylmethoxy)-isoxazole-5-carboxylic acid isopropyl-amide

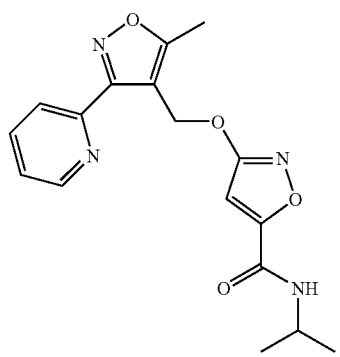

a) (E)- and/or (Z)-Pyridine-2-carbaldehyde oxime

To a suspension of 2-pyridinecarboxaldehyde (53.6 g, 500 mmol) and hydroxylamine hydrochloride (38.2 g, 544 mmol) in ethanol (36 mL) and water (69 mL) was added ice (205 g). Then an aqueous solution of sodium hydroxide (32%, 115 mL, 1.24 mol) was added dropwise within a 10 min period (temperature rises from −8° C. to +7° C.) whereupon most of the solid dissolves. After 1 h stirring at room temperature the resulting mixture was then acidified with HCl (5 N). The mixture was then extracted with dichloromethane to afford the title compound (47.7 g, 78%) which was obtained as an off white solid. MS: m/e=123.3 [M+H]$^+$.

b) 5-Methyl-3-pyridin-2-yl-isoxazole-4-carboxylic acid ethyl ester

To a suspension of N-chlorosuccinimide (6.0 g, 33 mmol) in chloroform (20 mL) was added pyridine (0.26 mL, 3.3 mmol) and a solution of (E)- and/or (Z)-pyridine-2-carbaldehyde oxime (4.0 g, 33 mmol) in chloroform (103 mL) during 15 min at ambient temperature. After stirring for 30 min at this temperature a solution of ethyl (E)-3-(1-pyrrolidino)-2-butenoate (6.0 g, 33 mmol) in chloroform (4 mL) was added. The resulting suspension was warmed to 50° C. and a solution of triethylamine (12 mL, 86 mmol) in chloroform (10 mL) was added dropwise over a period of 1 h. Stirring was continued for 0.5 h at 50° C. and for 30 h at room temperature. The dark brown solution was washed with water (100 mL) and the aqueous layers were extracted with dichloromethane (50 mL) and dried over sodium sulfate and evaporated. Purification by chromatography (silica, heptane:ethyl acetate 8:2 to 1:1) afforded the title compound (4.43 g, 58%) as a yellow oil. MS: m/e=233.3 [M+H]$^+$.

c) (5-Methyl-3-pyridin-2-yl-isoxazol-4-yl)-methanol

To a solution of 5-methyl-3-pyridin-2-yl-isoxazole-4-carboxylic acid ethyl ester (4.1 g, 18 mmol) in THF (229 mL) at 0° C. was added lithium aluminium hydride (367 mg, 10 mmol). And the resulting mixture stirred for 1 h at room temperature. Water (1.9 mL) was added carefully followed by aqueous sodium hydroxide (15%, 1.9 mL) and water (0.54 mL). The resulting suspension was stirred for 15 min at ambient temperature and filtered over Hyflo®. Concentration and trituration with heptane afforded the title compound (2.88 g, 86%) as a light yellow solid. MS: m/e=191.3 [M+H]$^+$.

d) 3-(5-Methyl-3-pyridin-2-yl-isoxazol-4-ylmethoxy)-isoxazole-5-carboxylic acid methyl ester To a solution of (5-methyl-3-pyridin-2-yl-isoxazol-4-yl)-methanol (465 mg, 2.44 mmol) in THF (10 mL) was added 3-oxo-2,3-dihydro-isoxazole-5-carboxylic acid methyl ester (350 mg, 2.45 mmol) and triphenylphosphine (769 mg, 2.93 mmol) at 0° C. under an argon atmosphere. Then diethyl azodicarboxylate (~40% in toluene, 1.23 mL, 2.68 mmol) was added and the reaction mixture was stirred for 1 h at 0° C. and then overnight at room temperature. Concentration and purification by chromatography (silica, heptane:ethyl acetate=4:1 to 1:4) afforded the title compound (443 mg, 57%) as a white solid. MS: m/e=316.2 [M+H]$^+$.

e) 3-(5-Methyl-3-pyridin-2-yl-isoxazol-4-ylmethoxy)-isoxazole-5-carboxylic acid isopropyl-amide To a solution of 3-(5-methyl-3-pyridin-2-yl-isoxazol-4-ylmethoxy)-isoxazole-5-carboxylic acid methyl ester (100 mg, 0.32 mmol) and isopropyl amine (22 mg, 0.37 mmol) in toluene (1 mL) was added 1,5,7-triazabicyclo[4.4.0]dec-5-ene (26 mg, 0.19 mmol) and the reaction stirred under argon for 3 h at 50° C. Then the mixture was evaporated and the residue purified by chromatography (silica, heptane:ethyl acetate=4:1 to 1:1) to afford the title compound (95 mg, 83%) which was obtained as an off-white solid. MS: m/e=343.2 [M+H]$^+$.

Example 15

3-(5-Methyl-3-pyridin-2-yl-isoxazol-4-ylmethoxy)-isoxazole-5-carboxylic acid (2-hydroxy-ethyl)-amide As described for example 14e, 3-(5-methyl-3-pyridin-2-yl-isoxazol-4-ylmethoxy)-isoxazole-5-carboxylic acid methyl ester (100 mg, 0.32 mmol) was converted, using ethanolamine (23 mg, 0.38 mmol) instead of isopropyl amine, to the title compound (90 mg, 82%) which was obtained as a white solid after purification by chromatography (silica, dichloromethane:methanol=1:0 to 9:1). MS: m/e=345.2 [M+H]$^+$.

Example 16

3-(5-Methyl-3-pyridin-2-yl-isoxazol-4-ylmethoxy)-isoxazole-5-carboxylic acid (tetrahydro-furan-3-yl)-amide

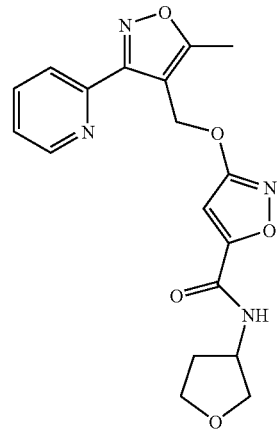

As described for example 14e, 3-(5-methyl-3-pyridin-2-yl-isoxazol-4-ylmethoxy)-isoxazole-5-carboxylic acid methyl ester (100 mg, 0.32 mmol) was converted, using 4-aminotetrahydropyran (33 mg, 0.38 mmol) instead of isopropyl amine, to the title compound (15 mg, 13%) which was obtained as a white solid after purification by chromatography (silica, heptane:ethyl acetate=4:1 to 1:4). MS: m/e=371.1 [M+H]$^+$.

Example 17

3-(5-Methyl-3-pyridin-2-yl-isoxazol-4-ylmethoxy)-isoxazole-5-carboxylic acid (2,2,2-trifluoro-ethyl)-amide

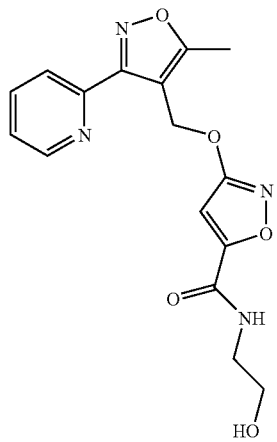

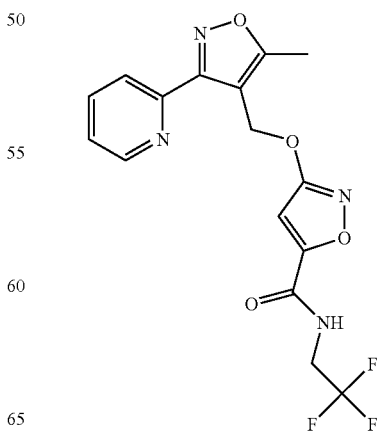

As described for example 14e, 3-(5-methyl-3-pyridin-2-yl-isoxazol-4-ylmethoxy)-isoxazole-5-carboxylic acid methyl ester (100 mg, 0.32 mmol) was converted, using 2,2,2-trifluoroethylamine (38 mg, 0.38 mmol) instead of isopropyl amine, to the title compound (77 mg, 64%) which was obtained as a white solid after purification by chromatography (silica, heptane:ethyl acetate=4:1 to 1:4). MS: m/e=383.1 [M+H]⁺.

Example 18

3-(5-Methyl-3-pyridin-2-yl-isoxazol-4-ylmethoxy)-isoxazole-5-carboxylic acid N',N'-dimethyl-hydrazide

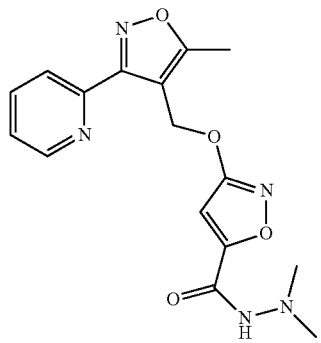

A solution of trimethylaluminium (2 M in toluene, 0.6 mL, 1.3 mmol) was added dropwise (exothermic) to a solution of N,N-dimethylhydrazine (76 mg, 1.3 mmol) in dioxane (3 mL) and the resulting mixture was stirred at room temperature for 1 h. Then a solution of 3-(5-methyl-3-pyridin-2-yl-isoxazol-4-ylmethoxy)-isoxazole-5-carboxylic acid methyl ester (100 mg, 0.32 mmol) in dioxane (2 mL) was added. The resulting mixture was then heated at 85-90° C. overnight, cooled to room temperature and poured into Seignette's salt and extracted with ethyl acetate which was then washed with brine, dried over sodium sulfate and evaporated. Purification by chromatography (silica, dichloromethane:methanol=9:1 to 7:3) afforded the title compound (86 mg, 79%) which was obtained as a white solid. MS: m/e=344.2 [M+H]⁺.

Example 19

3-(5-Methyl-3-pyridin-2-yl-isoxazol-4-ylmethoxy)-isoxazole-5-carboxylic acid morpholin-4-ylamide

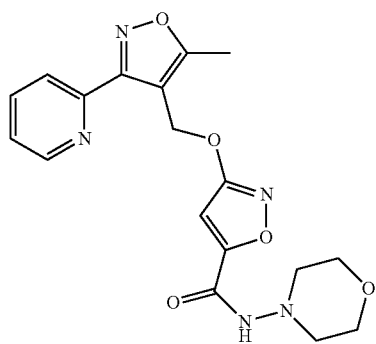

As described for example 18, 3-(5-methyl-3-pyridin-2-yl-isoxazol-4-ylmethoxy)-isoxazole-5-carboxylic acid methyl ester (100 mg, 0.33 mmol) was converted, using 4-aminomorpholine (136 mg, 1.3 mmol) instead of N,N-dimethylhydrazine, to the title compound (91 mg, 71%) which was obtained as a white solid after purification by chromatography (silica, dichloromethane:methanol=9:1 to 7:3). MS: m/e=386.2 [M+H]⁺.

Example 20

3-(5-Methyl-3-pyridin-2-yl-isoxazol-4-ylmethoxy)-isoxazole-5-carboxylic acid piperidin-1-ylamide

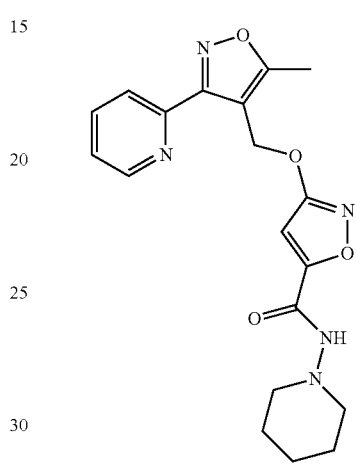

As described for example 18, 3-(5-methyl-3-pyridin-2-yl-isoxazol-4-ylmethoxy)-isoxazole-5-carboxylic acid methyl ester (100 mg, 0.33 mmol) was converted, using 1-aminopiperidine (127 mg, 1.27 mmol) instead of N,N-dimethylhydrazine, to the title compound (83 mg, 68%) which was obtained as a white solid after purification by chromatography (silica, dichloromethane:methanol=9:1 to 7:3). MS: m/e=384.2 [M+H]⁺.

Example 21

3-(5-Methyl-3-pyridin-2-yl-isoxazol-4-ylmethoxy)-isoxazole-5-carboxylic acid pyrrolidin-1-ylamide

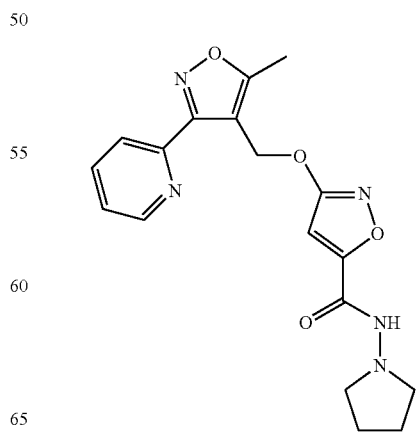

a) 3-(5-Methyl-3-pyridin-2-yl-isoxazol-4-yl-methoxy)-isoxazole-5-carboxylic acid To a solution of 3-(5-methyl-3-pyridin-2-yl-isoxazol-4-yl-methoxy)-isoxazole-5-carboxylic acid methyl ester (450 mg, 1.43 mmol) in dioxane (5 mL) was added aqueous sodium hydroxide (2 N, 3 mL). After heating at reflux for 1 h the mixture was cooled to room temperature and acidified with HCl (4 N, 2 mL). Purification by filtration and drying afforded the title compound (400 mg, 93%) which was obtained as a white solid. MS: m/e=300.1 [M–H]⁻.

b) 3-(5-Methyl-3-pyridin-2-yl-isoxazol-4-yl-methoxy)-isoxazole-5-carboxylic acid pyrrolidin-1-ylamide To a solution of 3-(5-methyl-3-pyridin-2-yl-isoxazol-4-yl-methoxy)-isoxazole-5-carboxylic acid (100 mg, 0.33 mmol) in DMF (5 mL) were added 2-(1H-benzotriazole-1-yl)-1,1,3,3-tetramethyluronium tetrafluoroborate (160 mg, 0.5 mmol), N,N-diisopropyl ethyl amine (280 µL, 1.7 mmol) and N-aminopyrrolidine HCl (61 mg, 0.50 mmol). The resulting reaction mixture was for 4 h at room temperature. Concentration and purification by chromatography (silica, dichloromethane:methanol=1:0 to 8.5:1.5) afforded the title compound (70 mg, 57%) as a white solid. MS: m/e=370.2 [M+H]⁺.

Example 22

3-[3-(5-Fluoro-pyridin-2-yl)-5-methyl-isoxazol-4-ylmethoxy]-isoxazole-5-carboxylic acid isopropylamide

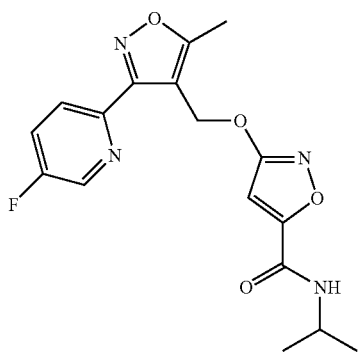

a) 5-Fluoro-pyridine-2-carbaldehyde oxime

To a solution of 5-fluoro-2-formylpyridine (5.0 g, 41 mmol) and hydroxylamine hydrochloride (3.06 g, 44 mmol) in ethanol (3.2 mL) and water (9.6 mL) was added ice (18.6 g). Then a solution of NaOH (4.0 g, 100 mmol) in water (4.6 mL) was added dropwise over 10 min keeping the temperature between –5° C. and 5° C. The reaction mixture was then stirred at room temperature for 30 min. Then HCl (4 N) was added to acidify the mixture and the resulting precipitate was filtered off and washed with the water to afford the title compound (4.41 g, 79%) as a light brown solid. MS: m/e=141.0 [M+H]⁺.

b) 3-(5-Fluoro-pyridin-2-yl)-5-methyl-isoxazole-4-carboxylic acid ethyl ester To a suspension of N-chlorosuccinimide (4.63 g, 35 mmol) in chloroform (21 mL) was added pyridine (0.28 mL, 3.5 mmol) and a solution of 5-fluoro-pyridine-2-carbaldehyde oxime (4.86 g, 35 mmol) in chloroform (110 mL) during 15 min at room temperature. After stirring for 30 min at this temperature a solution of ethyl (E)-3-(1-pyrrolidino)-2-butenoate (6.36 g, 35 mmol) in chloroform (4.4 mL) was added. The resulting suspension was warmed to 50° C. and a solution of triethylamine (4.83 mL, 35 mmol) in chloroform (4.4 mL) was added dropwise over a period of 30 min. Stirring was continued for 1.5 h at 50° C. and then cooled to ambient temperature. The solution was then diluted with ice-water (200 mL) and the aqueous layers were extracted with dichloromethane (50 mL) and dried over sodium sulfate and evaporation to give a dark brown oil. Purification by chromatography (silica, heptane:ethyl acetate=100:0 to 20:80) afforded the title compound (5.83 g, 67%) as yellow oil. MS: m/e=251.1 [M+H]⁺.

c) [3-(5-Fluoro-pyridin-2-yl)-5-methyl-isoxazol-4-yl]-methanol

To a solution of 3-(5-fluoro-pyridin-2-yl)-5-methyl-isoxazole-4-carboxylic acid ethyl ester (2.5 g, 10 mmol) in dry THF (34 mL), cooled to 0° C., was added lithiumaluminiumhydride (209 mg, 2.3 mmol) portionwise. After allowing to warm up to room temperature over 1 h, the mixture was cooled to 0° C. and water (0.2 mL) was added carefully followed by aqueous sodium hydroxide (15%, 0.2 mL) and water (0.6 mL). The resulting suspension was stirred for 4 h at ambient temperature and filtered over Hyflo®. The filtrate was then concentrated and purification by chromatography (silica, heptane:ethyl acetate=50:50 to 0:100) afforded the title compound (1.47 g, 71%) as a light yellow solid. MS: m/e=209.1 [M+H]⁺.

d) 3-[3-(5-Fluoro-pyridin-2-yl)-5-methyl-isoxazol-4-ylmethoxy]-isoxazole-5-carboxylic acid methyl ester To a solution of [3-(5-fluoro-pyridin-2-yl)-5-methyl-isoxazol-4-yl]-methanol (438 mg, 2.1 mmol) in THF (10 mL) was added 3-oxo-2,3-dihydro-isoxazole-5-carboxylic acid methyl ester (300 mg, 2.1 mmol) and triphenylphosphine (658 mg, 2.1 mmol) at room temperature under an argon atmosphere. Then diethyl azodicarboxylate (~40% in toluene, 1.1 mL, 2.5 mmol) was added and the reaction mixture was stirred for 3 h at room temperature. Concentration and purification by chromatography (silica, dichloromethane:methanol=4:1 to 1:4) afforded the title compound (431 mg, 62%) as a white solid. MS: m/e=334.2 [M+H]⁺.

e) 3-[3-(5-Fluoro-pyridin-2-yl)-5-methyl-isoxazol-4-ylmethoxy]-isoxazole-5-carboxylic acid isopropylamide As described for example 14e, 3-[3-(5-fluoro-pyridin-2-yl)-5-methyl-isoxazol-4-ylmethoxy]-isoxazole-5-carboxylic acid methyl ester (100 mg, 0.3 mmol), instead of 3-(5-methyl-3-pyridin-2-yl-isoxazol-4-ylmethoxy)-isoxazole-5-carboxylic acid methyl ester, was converted, using isopropyl amine (21 mg, 0.36 mmol), to the title compound (95 mg, 88%) which was obtained as a white solid after purification by chromatography (silica, dichloromethane:methanol=1:0 to 9:1). MS: m/e=361.2 [M+H]+.

Example 23

3-[3-(5-Fluoro-pyridin-2-yl)-5-methyl-isoxazol-4-ylmethoxy]-isoxazole-5-carboxylic acid (2-hydroxy-ethyl)-amide

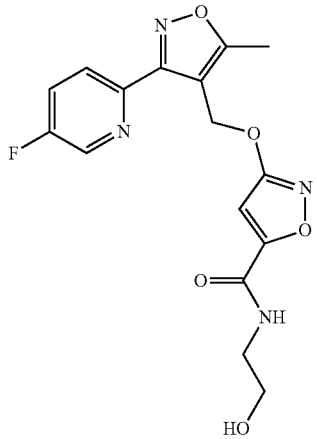

As described for example 22e, 33-[3-(5-fluoro-pyridin-2-yl)-5-methyl-isoxazol-4-ylmethoxy]-isoxazole-5-carboxylic acid methyl ester (100 mg, 0.3 mmol) was converted, using ethanolamine (22 mg, 0.36 mmol) instead of isopropyl amine, to the title compound (76 mg, 70%) which was obtained as a white solid after purification by chromatography (silica, dichloromethane:methanol=1:0 to 9:1). MS: m/e=363.1 [M+H]+.

Example 24

3-(3-Butyl-5-methyl-isoxazol-4-ylmethoxy)-isoxazole-5-carboxylic acid (2-hydroxy-ethyl)-amide

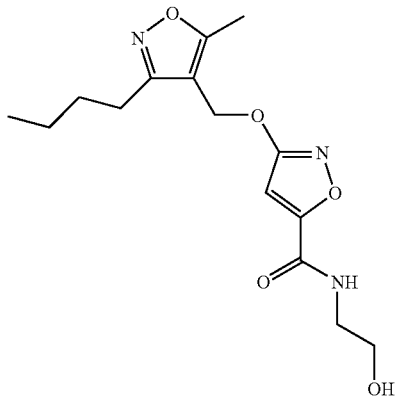

a) 3-(3-Butyl-5-methyl-isoxazol-4-ylmethoxy)-isoxazole-5-carboxylic acid methyl ester To a solution of 3-butyl-5-methyl-4-isoxazolyl-methanol (1.5 g, 8.9 mmol) in THF (30 mL) was added 3-oxo-2,3-dihydro-isoxazole-5-carboxylic acid methyl ester (1.27 g, 8.9 mmol) and triphenylphosphine (2.79 g, 10.6 mmol) at 0° C. under an argon atmosphere. Then diethyl azodicarboxylate (~40% in toluene, 4.25 mL, 9.8 mmol) was added and the reaction mixture was stirred overnight at room temperature. Concentration and purification by chromatography (silica, heptane:ethyl acetate=4:1 to 1:1) afforded the title compound (1.44 g, 55%) as a colourless liquid. MS: m/e=295.0 [M+H]+.

b) 3-(3-Butyl-5-methyl-isoxazol-4-ylmethoxy)-isoxazole-5-carboxylic acid (2-hydroxy-ethyl)-amide As described for example 14e, 3-(3-butyl-5-methyl-isoxazol-4-ylmethoxy)-isoxazole-5-carboxylic acid methyl ester (201 mg, 0.68 mmol), instead of 3-(5-methyl-3-pyridin-2-yl-isoxazol-4-ylmethoxy)-isoxazole-5-carboxylic acid methyl ester, was converted, using ethanolamine (50 mg, 0.82 mmol), instead of isopropyl amine, to the title compound (103 mg, 47%) which was obtained as a colourless gum after purification by chromatography (silica, heptane:ethyl acetate=1:1 to 0:1). MS: m/e=324.3 [M+H]+.

Example 25

3-(3-Butyl-5-methyl-isoxazol-4-ylmethoxy)-isoxazole-5-carboxylic acid (2-hydroxy-1-methyl-ethyl)-amide

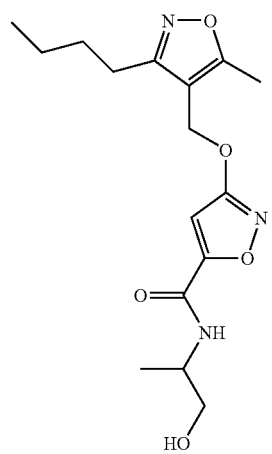

As described for example 24b, 3-(3-butyl-5-methyl-isoxazol-4-ylmethoxy)-isoxazole-5-carboxylic acid methyl ester (201 mg, 0.68 mmol), was converted using 1-hydroxymethylethylamine (62 mg, 0.82 mmol), instead of ethanolamine, to the title compound (142 mg, 62%) which was obtained as a colourless gum after purification by chromatography (silica, heptane:ethyl acetate=1:1 to 0:1). MS: m/e=338.5 [M+H]+.

Example 26

3-(3-Butyl-5-methyl-isoxazol-4-ylmethoxy)-isoxazole-5-carboxylic acid ((S)-2-hydroxy-1-methylethyl)-amide

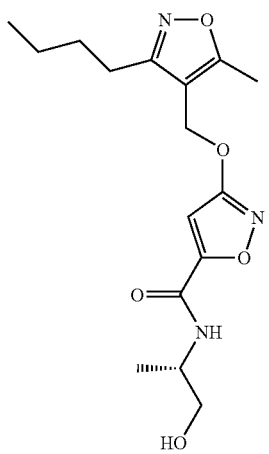

As described for example 24b, 3-(3-butyl-5-methyl-isoxazol-4-ylmethoxy)-isoxazole-5-carboxylic acid methyl ester (199 mg, 0.68 mmol), was converted using (S)-1-hydroxymethylethylamine (61 mg, 0.81 mmol), instead of ethanolamine, to the title compound (148 mg, 65%) which was obtained as a colourless gum after purification by chromatography (silica, heptane:ethyl acetate=1:1 to 0:1). MS: m/e=338.4 [M+H]+.

Example 27

3-(3-Butyl-5-methyl-isoxazol-4-ylmethoxy)-isoxazole-5-carboxylic acid ((R)-2-hydroxy-1-methylethyl)-amide

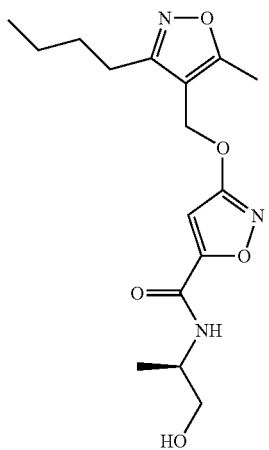

As described for example 24b, 3-(3-butyl-5-methyl-isoxazol-4-ylmethoxy)-isoxazole-5-carboxylic acid methyl ester (199 mg, 0.68 mmol), was converted using (R)-1-hydroxymethylethylamine (61 mg, 0.81 mmol), instead of ethanolamine, to the title compound (137 mg, 60%) which was obtained as a colourless gum after purification by chromatography (silica, heptane:ethyl acetate=1:1 to 0:1). MS: m/e=338.5 [M+H]+.

Example 28

3-(3-Butyl-5-methyl-isoxazol-4-ylmethoxy)-isoxazole-5-carboxylic acid isopropylamide

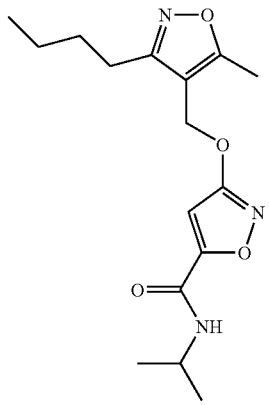

A solution of trimethylaluminium (2 M in toluene, 1.02 mL, 2.0 mmol) was added dropwise (exothermic) to a solution of isopropyl amine (121 mg, 2.0 mmol) in dioxane (6 mL) and the resulting mixture was stirred at room temperature for 1 h. Then 3-(3-butyl-5-methyl-isoxazol-4-ylmethoxy)-isoxazole-5-carboxylic acid methyl ester (200 mg, 0.68 mmol) was added. The resulting mixture was then heated at 70° C. for 3 h and then cooled to room temperature and then poured into Seignette's salt and extracted with ethyl acetate which was then washed with brine, dried over sodium sulfate and evaporated. Purification by chromatography (silica, heptane:ethyl acetate=4:1 to 4:1) afforded the title compound (204 mg, 93%) which was obtained as a colourless oil. MS: m/e=322.4 [M+H]+.

Example 29

3-(3-Butyl-5-methyl-isoxazol-4-ylmethoxy)-isoxazole-5-carboxylic acid (tetrahydro-furan-3-yl)-amide

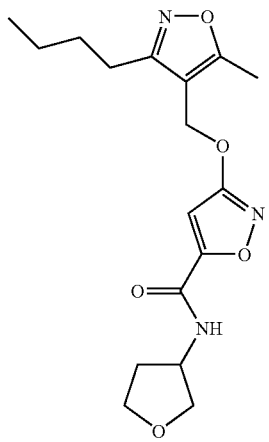

As described for example 28, 3-(3-butyl-5-methyl-isoxazol-4-ylmethoxy)-isoxazole-5-carboxylic acid methyl ester (377 mg, 1.28 mmol), was converted using 3-aminotetrahydrofuran (335 mg, 3.84 mmol), instead of isopropyl amine, to the title compound (368 mg, 82%) which was obtained as a colourless gum after purification by chromatography (silica, heptane:ethyl acetate=4:1 to 4:1). MS: m/e=350.4 [M+H]$^+$.

Example 30

(R or S)-3-(3-Butyl-5-methyl-isoxazol-4-ylmethoxy)-isoxazole-5-carboxylic acid (tetrahydro-furan-3-yl)-amide

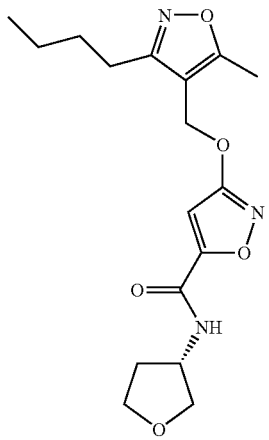

The stereoisomers of 3-(3-butyl-5-methyl-isoxazol-4-ylmethoxy)-isoxazole-5-carboxylic acid (tetrahydro-furan-3-yl)-amide (example 29, 296 mg) in ethanol:heptane (1:1, 8 mL) were separated using a 5×50 cm Chiralpak AD column at room temperature using an isopropanol:heptane (1.5:8.5) mobile phase with UV detection at 220 nM. The least polar component (−ve sign of rotation) was obtained as a white solid (100 mg).

Example 31

(S or R)-3-(3-Butyl-5-methyl-isoxazol-4-ylmethoxy)-isoxazole-5-carboxylic acid (tetrahydro-furan-3-yl)-amide

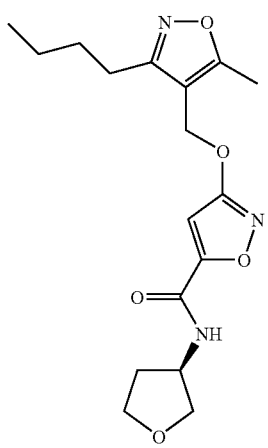

The stereoisomers of 3-(3-butyl-5-methyl-isoxazol-4-ylmethoxy)-isoxazole-5-carboxylic acid (tetrahydro-furan-3-yl)-amide (example 29, 296 mg) in ethanol:heptane (1:1, 8 mL) were separated using a 5×50 cm Chiralpak AD column at room temperature using an isopropanol:heptane (1.5:8.5) mobile phase with UV detection at 220 nM. The most polar component (+ve sign of rotation) was obtained as a colourless gum (116 mg).

Example 32

3-(3-Butyl-5-methyl-isoxazol-4-ylmethoxy)-isoxazole-5-carboxylic acid N',N'-dimethyl-hydrazide

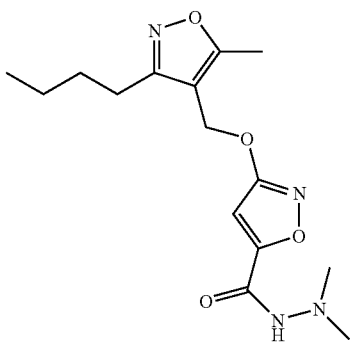

As described for example 28, 3-(3-butyl-5-methyl-isoxazol-4-ylmethoxy)-isoxazole-5-carboxylic acid methyl ester (110 mg, 0.37 mmol), was converted using N,N-dimethylhydrazine (90 mg, 1.5 mmol), instead of isopropyl amine, to the title compound (120 mg, 99%) which was obtained as a colourless oil after purification by chromatography (silica, dichloromethane:methanol=1:0 to 9:1). MS: m/e=323.3 [M+H]$^+$.

Example 33

3-(3-Butyl-5-methyl-isoxazol-4-ylmethoxy)-isoxazole-5-carboxylic acid morpholin-4-ylamide

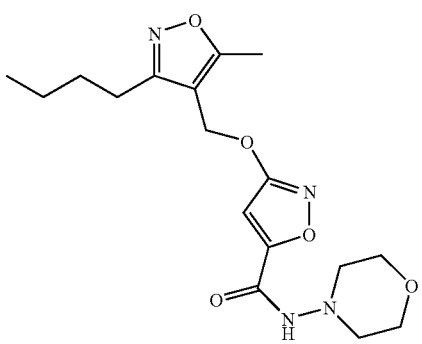

As described for example 28, 3-(3-butyl-5-methyl-isoxazol-4-ylmethoxy)-isoxazole-5-carboxylic acid methyl ester (110 mg, 0.37 mmol), was converted using 4-aminomorpholine (153 mg, 1.5 mmol), instead of isopropyl amine, to the title compound (83 mg, 61%) which was obtained as a colourless oil after purification by chromatography (silica, dichloromethane:methanol=1:0 to 9:1). MS: m/e=365.3 [M+H]$^+$.

Example 34

3-(5-Methyl-3-phenyl-isoxazol-4-ylmethoxy)-isothiazole-5-carboxylic acid isopropylamide

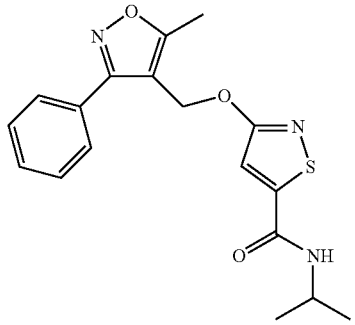

a) 3-(5-Methyl-3-phenyl-isoxazol-4-ylmethoxy)-isothiazole-5-carboxylic acid methyl ester To a solution of (5-methyl-3-phenyl-isoxazol-4-yl)-methanol (350 mg, 2.2 mmol) in THF (30 mL) was added 3-hydroxy-isothiazole-5-carboxylic acid methyl ester (416 mg, 2.2 mmol) and triphenylphosphine (692 mg, 2.4 mmol) at 0° C. under an argon atmosphere. Then diethyl azodicarboxylate (~40% in toluene, 1.05 mL, 2.4 mmol) was added and the reaction mixture was stirred overnight at room temperature. Concentration and purification by chromatography (silica, heptane:ethyl acetate=9:1 to 0:1) afforded the title compound (567 mg, 78%) as a colourless oil. MS: m/e=331.1 [M+H]$^+$.

b) 3-(5-Methyl-3-phenyl-isoxazol-4-ylmethoxy)-isothiazole-5-carboxylic acid isopropylamide As described for example 14e, 3-(5-methyl-3-phenyl-isoxazol-4-ylmethoxy)-isothiazole-5-carboxylic acid methyl ester (100 mg, 0.3 mmol), instead of 3-(5-methyl-3-pyridin-2-yl-isoxazol-4-ylmethoxy)-isoxazole-5-carboxylic acid methyl ester, was converted, using isopropyl amine (21 mg, 0.36 mmol), to the title compound (74 mg, 68%) which was obtained as a white solid after purification by chromatography (silica, dichloromethane:methanol=1:0 to 9:1). MS: m/e=358.1 [M+H]$^+$.

Example 35

3-(5-Methyl-3-phenyl-isoxazol-4-ylmethoxy)-isothiazole-5-carboxylic acid (2-hydroxy-ethyl)-amide

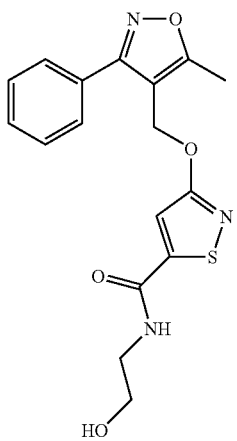

As described for example 34, 3-(5-methyl-3-phenyl-isoxazol-4-ylmethoxy)-isothiazole-5-carboxylic acid methyl ester (100 mg, 0.3 mmol), was converted, using ethanolamine (21 mg, 0.34 mmol), instead of isopropyl amine, to the title compound (60 mg, 58%) which was obtained as a white solid after purification by chromatography (silica, dichloromethane:methanol=1:0 to 9:1). MS: m/e=360.1 [M+H]$^+$.

Example 36

3-(5-Methyl-3-pyridin-2-yl-isoxazol-4-ylmethoxy)-isothiazole-5-carboxylic acid isopropyl-amide

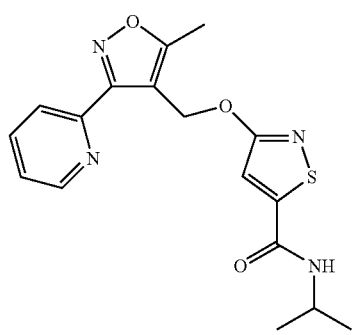

a) 3-(5-Methyl-3-pyridin-2-yl-isoxazol-4-ylmethoxy)-isothiazole-5-carboxylic acid methyl ester To a solution of (5-methyl-3-pyridin-2-yl-isoxazol-4-yl)-methanol (360 mg, 1.9 mmol) in THF (10 mL) was added 3-hydroxy-isothiazole-5-carboxylic acid methyl ester (300 mg, 1.9 mmol) and triphenylphosphine (594 mg, 1.9 mmol) at 0° C. under an argon atmosphere. Then diethyl azodicarboxylate (~40% in toluene, 0.95 mL, 1.9 mmol) was added and the reaction mixture was stirred overnight at room temperature. Concentration and purification by chromatography (silica, heptane:ethyl acetate=4:1 to 1:4) afforded the title compound (350 mg, 56%) as a white solid. MS: m/e=332.2 [M+H]$^+$.

b) 3-(5-Methyl-3-pyridin-2-yl-isoxazol-4-ylmethoxy)-isothiazole-5-carboxylic acid isopropyl-amide As described for example 14e, 3-(5-methyl-3-pyridin-2-yl-isoxazol-4-ylmethoxy)-isothiazole-5-carboxylic acid methyl ester (100 mg, 0.32 mmol), instead of 3-(5-methyl-3-pyridin-2-yl-isoxazol-4-ylmethoxy)-isoxazole-5-carboxylic acid methyl ester, was converted, using isopropyl amine (22 mg, 0.37 mmol), to the title compound (95 mg, 83%) which was obtained as an off white solid after purification by chromatography (silica, heptane:ethyl acetate=4:1 to 1:4). MS: m/e=343.2 [M+H]$^+$.

Example 37

3-(5-Methyl-3-pyridin-2-yl-isoxazol-4-ylmethoxy)-isothiazole-5-carboxylic acid (2-hydroxy-ethyl)-amide

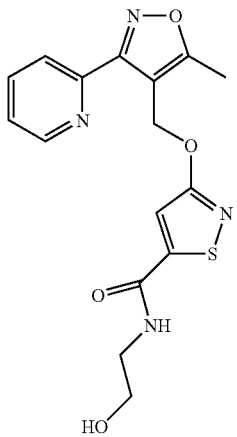

As described for example 36b, 3-(5-methyl-3-pyridin-2-yl-isoxazol-4-ylmethoxy)-isothiazole-5-carboxylic acid methyl ester (100 mg, 0.32 mmol), was converted, using ethanolamine (23 mg, 0.38 mmol), instead of isopropyl amine, to the title compound (90 mg, 82%) which was obtained as a white solid after purification by chromatography (silica, dichloromethane:methanol=1:0 to 9:1). MS: m/e=345.2 [M+H]$^+$.

Example 38

3-[3-(5-Fluoro-pyridin-2-yl)-5-methyl-isoxazol-4-ylmethoxy]-isothiazole-5-carboxylic acid isopropylamide

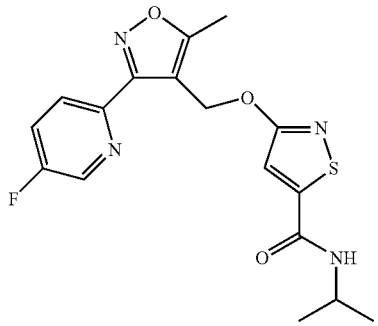

a) 3-[3-(5-Fluoro-pyridin-2-yl)-5-methyl-isoxazol-4-ylmethoxy]-isothiazole-5-carboxylic acid methyl ester To a solution of [3-(5-fluoro-pyridin-2-yl)-5-methyl-isoxazol-4-yl]-methanol (458 mg, 2.2 mmol) in THF (10 mL) was added 3-hydroxy-isothiazole-5-carboxylic acid methyl ester (350 mg, 1.9 mmol) and triphenylphosphine (692 mg, 2.6 mmol) at 0° C. under an argon atmosphere. Then diethyl azodicarboxylate (~40% in toluene, 1.05 mL, 2.4 mmol) was added and the reaction mixture was stirred overnight at room temperature. Concentration and purification by chromatography (silica, heptane:ethyl acetate=4:1 to 0:1) afforded the title compound (488 mg, 64%) as a white solid. MS: m/e=350.1 [M+H]$^+$.

b) 3-[3-(5-Fluoro-pyridin-2-yl)-5-methyl-isoxazol-4-ylmethoxy]-isothiazole-5-carboxylic acid isopropylamide As described for example 14e, 3-[3-(5-fluoro-pyridin-2-yl)-5-methyl-isoxazol-4-ylmethoxy]-isothiazole-5-carboxylic acid methyl ester (120 mg, 0.34 mmol), instead of 3-(5-methyl-3-pyridin-2-yl-isoxazol-4-ylmethoxy)-isoxazole-5-carboxylic acid methyl ester, was converted, using isopropyl amine (24 mg, 0.41 mmol), to the title compound (99 mg, 77%) which was obtained as a white solid after purification by chromatography (silica, heptane:ethyl acetate=4:1 to 1:4). MS: m/e=377.2 [M+H]$^+$.

Example 39

3-[3-(5-Fluoro-pyridin-2-yl)-5-methyl-isoxazol-4-ylmethoxy]-isothiazole-5-carboxylic acid (2-hydroxy-ethyl)-amide

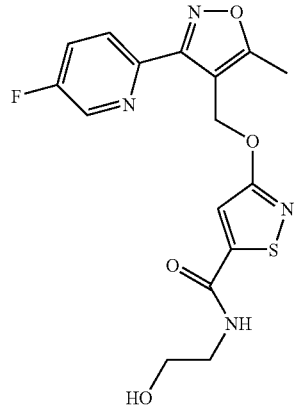

As described for example 38b, 3-[3-(5-fluoro-pyridin-2-yl)-5-methyl-isoxazol-4-ylmethoxy]-isothiazole-5-carboxylic acid methyl ester (120 mg, 0.34 mmol), was converted, using ethanolamine (25 mg, 0.41 mmol), instead of isopropyl amine, to the title compound (91 mg, 70%) which was obtained as a white solid after purification by chromatography (silica, dichloromethane:methanol=97.5:2.5 to 9:1). MS: m/e=379.3 [M+H]$^+$.

Example 40

3-[3-(5-Fluoro-pyridin-2-yl)-5-methyl-isoxazol-4-ylmethoxy]-isothiazole-5-carboxylic acid (tetrahydro-furan-3-yl)-amide

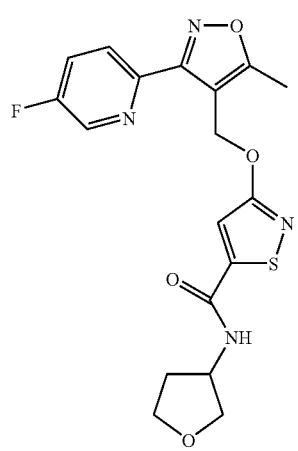

53

As described for example 38b, 3-[3-(5-fluoro-pyridin-2-yl)-5-methyl-isoxazol-4-ylmethoxy]-isothiazole-5-carboxylic acid methyl ester (120 mg, 0.34 mmol), was converted, using 3-aminotetrahydrofuran (36 mg, 0.41 mmol), instead of isopropyl amine, to the title compound (38 mg, 27%) which was obtained as a white solid after purification by chromatography (silica, heptane:ethyl acetate=75:25 to 25:75). MS: m/e=405.3 [M+H]$^+$.

Example 41

3-(3-Butyl-5-methyl-isoxazol-4-ylmethoxy)-isothiazole-5-carboxylic acid (tetrahydro-furan-3-yl)-amide

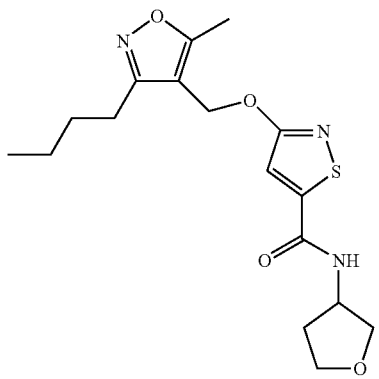

a) 3-(3-Butyl-5-methyl-isoxazol-4-ylmethoxy)-isothiazole-5-carboxylic acid methyl ester To a solution of 3-butyl-5-methyl-4-isoxazolyl-methanol (367 mg, 2.2 mmol) in THF (10 mL) was added 3-hydroxy-isothiazole-5-carboxylic acid methyl ester (345 mg, 2.2 mmol) and triphenylphosphine (622 mg, 2.4 mmol) at 0° C. under an argon atmosphere. Then diethyl azodicarboxylate (~40% in toluene, 1.04 mL, 2.4 mmol) was added and the reaction mixture was stirred overnight at room temperature. Concentration and purification by chromatography (silica, heptane:ethyl acetate=9:1 to 0:1) afforded the title compound (518 mg, 77%) as a colourless liquid. MS: m/e=311.2 [M+H]$^+$.

b) 3-(3-Butyl-5-methyl-isoxazol-4-ylmethoxy)-isothiazole-5-carboxylic acid (tetrahydro-furan-3-yl)-amide As described for example 14e, 3-(3-butyl-5-methyl-isoxazol-4-ylmethoxy)-isothiazole-5-carboxylic acid methyl ester (165 mg, 0.53 mmol), instead of 3-(5-methyl-3-pyridin-2-yl-isoxazol-4-ylmethoxy)-isoxazole-5-carboxylic acid methyl ester, was converted, using 3-aminotetrahydrofuran (56 mg, 0.64 mmol), instead of isopropyl amine, to the title compound (32 mg, 16%) which was obtained as a colourless gum after purification by chromatography (silica, heptane:ethyl acetate=4:1 to 0:1). MS: m/e=366.2 [M+H]$^+$.

54

Example 42

{3-[3-(4-Fluoro-phenyl)-5-methyl-isoxazol-4-ylmethoxy]-isoxazol-5-yl}-(2-oxa-6-aza-spiro[3.3]hept-6-yl)-methanone

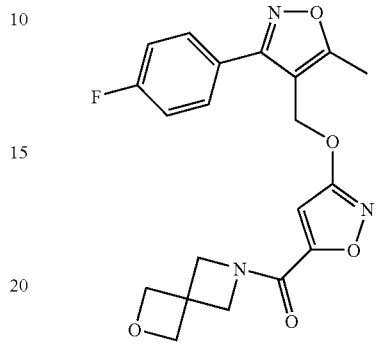

a) 3-[3-(4-Fluoro-phenyl)-5-methyl-isoxazol-4-ylmethoxy]-isoxazole-5-carboxylic acid methyl ester To a solution of [3-(4-fluoro-phenyl)-5-methyl-isoxazol-4-yl]-methanol (1.0 g, 4.8 mmol) in THF (70 mL) was added 3-oxo-2,3-dihydro-isoxazole-5-carboxylic acid methyl ester (0.69 g, 4.8 mmol) and triphenylphosphine (1.65 g, 6.3 mmol) at ambient temperature under an argon atmosphere. Then diethyl azodicarboxylate (2.7 mL, 6.3 mmol) was added at 4° C. and the reaction mixture was stirred for 3 h at room temperature. Concentration and purification by chromatography (SiO$_2$, heptane:ethyl acetate=100:0 to 7:3) afforded the title compound (958 mg, 60%) as a white solid. MS: m/e=333.2 [M+H]$^+$.

b) {3-[3-(4-Fluoro-phenyl)-5-methyl-isoxazol-4-ylmethoxy]-isoxazol-5-yl}-(2-oxa-6-aza-spiro[3.3]hept-6-yl)-methanone Trimethylaluminum (1.0 mL of a 2 M solution in hexane, 2 mmol) was slowly added to a solution of 2-oxa-6-azonia-spiro[3.3]heptane oxalate salt (100 mg, 0.53 mmol) in toluene (2 mL) at 0° C. and the resulting mixture stirred for 2 h at room temperature. Then a solution of 3-[3-(4-fluoro-phenyl)-5-methyl-isoxazol-4-ylmethoxy]-isoxazole-5-carboxylic acid methyl ester (200 mg, 0.6 mmol) in toluene (8 mL) was added dropwise and the resulting mixture heated at 110° C. for 3 h. After cooling to room temperature and extractive workup (ethyl acetate/aqueous saturated Seignette's salt solution) the organic phase was dried (Na$_2$SO$_4$) and filtered. Purification by chromatography (silica, dichloromethane:methanol=95:5 to 7:3) afforded the title compound (19 mg, 8%) as a colourless oil. MS: m/e=400.1 [M+H]$^+$.

Example 43

3-[3-(4-Fluoro-phenyl)-5-hydroxymethyl-isoxazol-4-ylmethoxy]-isoxazole-5-carboxylic acid isopropylamide

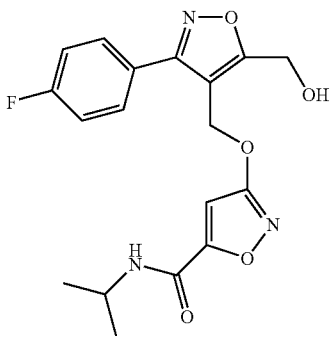

a) 3-(4-Fluoro-phenyl)-5-((E)-styryl)-isoxazole-4-carboxylic acid

To a solution of 3-(4-fluoro-phenyl)-5-methyl-isoxazole-4-carboxylic acid ethyl ester (20.0 g, 80.2 mmol) and benzaldehyde (8.19 mL, 80.2 mmol) in ethanol (113 mL) was added sodium ethoxide (2.71 M, 32.5 mL, 88.3 mmol) and the reaction mixture was heated under reflux for 1 h. Hydrochloric acid (1 N, 96.3 mL) was added and the resulting mixture was extracted with toluene. The solvent was then distilled off to afford the title compound (19.1 g, 77%) as a light yellow solid. MS: m/e=308.0 [M−H]⁻.

b) [3-(4-Fluoro-phenyl)-5-((E)-styryl)-isoxazol-4-yl]-methanol

To a solution of 3-(4-fluoro-phenyl)-5-((E)-styryl)-isoxazole-4-carboxylic acid (19.0 g, 61.4 mmol) and triethylamine (8.6 mL, 61.4 mmol) in THF (475 mL) was added at room temperature a solution of ethyl chloroformate (5.97 mL, 61.4 mmol) in THF (55 mL). After 1 h the triethylamine hydrochloride salt was filtered off and washed with a small amount of THF.

The mixture was added to a solution of sodium borohydride (6.05 g, 154 mmol) and water (55 mL). After stirring overnight at room temperature aqueous sodium hydroxide solution (1 N, 180 mL) was added. Extraction with tert-butylmethylether, removal of the solvent by distillation and chromatography (silica, dichloromethane:methanol=1:0 to 95:5) afforded the title compound (11.4 g, 63%) as a light yellow solid. MS: m/e=296.2 [M+H]⁺.

c) 3-[3-(4-Fluoro-phenyl)-5-((E)-styryl)-isoxazol-4-ylmethoxy]-isoxazole-5-carboxylic acid methyl ester A solution of methyl 3-hydroxy-5-isoxazolcarboxylate (4.2 g, 28.8 mmol) in THF (314 mL) was added to a solution of [3-(4-fluoro-phenyl-5-((E)-styryl)-isoxazol-4-yl]-methanol (8.5 g, 28.8 mmol) in THF (349 mL) containing triphenylphosphine (10.1 g, 37.4 mmol) at 5° C. and then DIAD (7.89 mL, 37.4 mmol) was added dropwise to the reaction mixture. The resulting mixture was then stirred overnight at room temperature. Evaporation of the mixture followed by chromatography (silica, ethyl acetate:heptane=1:3) afforded the title compound (6.84 g, 57%) as a light yellow solid. MS: m/e=479.0 [M+OAc]⁻.

d) 3-[5-((1S,2R)-1,2-Dihydroxy-2-phenyl-ethyl)-3-(4-fluoro-phenyl)-isoxazol-4-ylmethoxy]-isoxazole-5-carboxylic acid methyl ester Osmium (VIII) oxide (65.1 mL, 6.4 mmol), N-methylmorpholine N-oxide (1.93 g, 16 mmol) and de-ionized water (16.8 mL) were added at room temperature to a solution of 3-[3-(4-fluoro-phenyl)-5-((E)-styryl)-isoxazol-4-ylmethoxy]-isoxazole-5-carboxylic acid methyl ester (6.73 g, 16 mmol) in dioxane (67.3 mL) and the resulting mixture stirred overnight. The reaction mixture was then extracted with ethyl acetate and sodium thiosulfate, the organic phases were washed with brine, dried over sodium sulfate, filtered and evaporated. Purification by chromatography (silica, ethyl acetate:heptane=1:4 to 1:1) afforded the title compound (3.81 g, 52%) as a colourless oil. MS: m/e=453.0 [M+H]⁺.

e) 3-[3-(4-Fluoro-phenyl)-5-formyl-isoxazol-4-ylmethoxy]-isoxazole-5-carboxylic acid methyl ester Sodium (meta)periodate (2.68 g, 8.4 mmol) was added to a solution of 3-[5-((1S,2R)-1,2-dihydroxy-2-phenyl-ethyl)-3-(4-fluoro-phenyl)-isoxazol-4-ylmethoxy]-isoxazole-5-carboxylic acid methyl ester (3.8 g, 8.4 mmol) in THF (21 mL) and de-ionized water (4.3 mL) at 0° C. and the resulting mixture stirred overnight at 0° C. The reaction mixture was extracted with ethyl acetate the combined organic phases were washed with brine, dried over sodium sulfate, filtered and evaporated to afford the title compound (2.9 g, 100%) which was obtained as a colorless oil and used in the next step directly. MS: m/e=405.1 [M+OAc]⁻.

f) 3-[3-(4-Fluoro-phenyl)-5-hydroxymethyl-isoxazol-4-ylmethoxy]-isoxazole-5-carboxylic acid methyl ester Lithium borohydride (762.5 mg, 19.4 mmol) was added to a solution of 3-[3-(4-fluoro-phenyl)-5-formyl-isoxazol-4-ylmethoxy]-isoxazole-5-carboxylic acid methyl ester (2.9 g, 8.4 mmol) in methanol (168 mL) and the resulting mixture stirred for 1 h at room temperature. Citric acid (10%, 100 mL) was then added and the resulting mixture extracted with ethyl acetate. The combined organic phases were washed with brine, dried over sodium sulfate, filtered and evaporated. Purification by chromatography (silica, ethyl acetate:heptane=1:4 to 1:1) afforded the title compound (1.63 g, 48%) as a white solid. MS: m/e=407.2 [M+AcO]⁻.

g) 3-[3-(4-Fluoro-phenyl)-5-hydroxymethyl-isoxazol-4-ylmethoxy]-isoxazole-5-carboxylic acid isopropylamide Trimethylaluminum (0.57 mL of a 2 M solution in hexane, 1.15 mmol) was slowly added to a solution of isopropylamine (68.2 mg, 1.15 mmol) in dioxane (5.0 mL) and stirred at 80° C. for 1 h. Then a solution of 3-[3-(4-fluoro-phenyl)-5-hydroxymethyl-isoxazol-4-ylmethoxy]-isoxazole-5-carboxylic acid methyl ester (100 mg, 0.29 mmol) in dioxane (5.0 mL) was added dropwise. The mixture was stirred at 85° C. overnight. After cooling to room temperature and extractive workup (ethyl acetate/aqueous saturated Seignette's salt solution) the organic phase was dried (Na₂SO₄) and filtered. Purification by chromatography (silica, ethyl acetate:heptane=3:7 to 1:1) afforded the title compound (50 mg, 46%) as a white solid. MS: m/e=373.9 [M–H]⁻.

Example 44

3-[3-(4-Fluoro-phenyl)-5-hydroxymethyl-isoxazol-4-ylmethoxy]-isoxazole-5-carboxylic acid (tetrahydro-pyran-4-yl)-amide

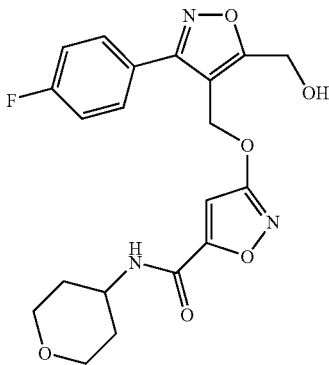

As described for example 43 g, 3-[3-(4-fluoro-phenyl)-5-hydroxymethyl-isoxazol-4-ylmethoxy]-isoxazole-5-carboxylic acid methyl ester (100 mg, 0.29 mmol) was converted, using 4-aminotetrahydropyran instead of isopropylamine, to the title compound (55 mg, 46%) which was obtained as a white solid after purification by chromatography (silica, dichloromethane:methanol=1:0 to 9:1). MS: m/e=416.1 [M–H]⁻.

Example 45

3-[3-(4-Fluoro-phenyl)-5-hydroxymethyl-isoxazol-4-ylmethoxy]-isoxazole-5-carboxylic acid (2,2,2-trifluoro-ethyl)-amide

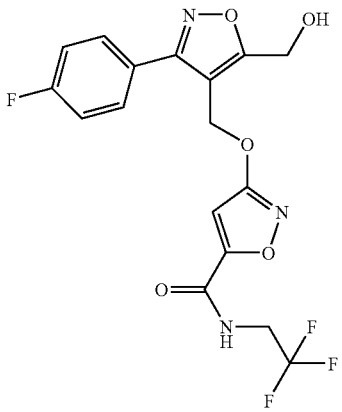

As described for example 43 g, 3-[3-(4-fluoro-phenyl)-5-hydroxymethyl-isoxazol-4-ylmethoxy]-isoxazole-5-carboxylic acid methyl ester (100 mg, 0.29 mmol) was converted, using 2,2,2-trifluoroethylamine instead of isopropylamine, to the title compound (25 mg, 21%) which was obtained as a white solid after purification by chromatography (silica, dichloromethane:methanol=1:0 to 9:1). MS: m/e=414.0 [M–H]⁻.

The invention claimed is:
1. A compound of formula I,

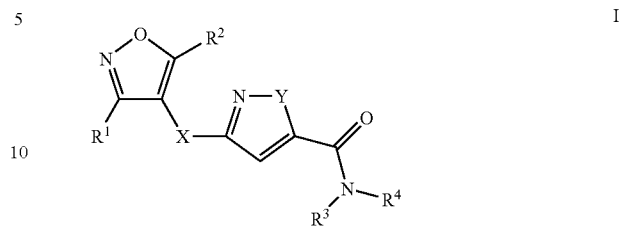

wherein
R¹ is lower alkyl, optionally substituted by halogen, cyano, hydroxy, lower-alkoxy or halogen-lower-alkoxy,
aryl, heteroaryl, cycloalkyl, or heterocyclyl; each of which is optionally substituted by halogen, cyano, hydroxy, lower alkyl, halogen-lower alkyl, cyano-lower alkyl, hydroxy-lower alkyl, lower alkyl-C(=O)OH, lower alkyl-C(=O)O-lower alkyl, lower alkyl-CO—NR⁵R⁶, lower alkyl-NR⁵R⁶, lower-alkoxy-lower alkyl, —CO-lower alkyl, —C(=O)OH, —C(=O)O-lower alkyl, —CONR⁵R⁶, —NR⁵R⁶, lower-alkoxy, halogen-lower-alkoxy, —SO₂-lower alkyl, —SO₂—NR⁵R⁶, cycloalkyl, phenyloxy or phenyl,
R² is lower alkyl optionally substituted by halogen, cyano, hydroxy, lower-alkoxy or halogen-lower-alkoxy,
R³ is lower alkyl, optionally substituted by carboxy, halogen or hydroxyl;
aryl, heteroaryl, cycloalkyl, or heterocyclyl; each of which is optionally substituted by carboxy, halogen, hydroxy or lower alkyl; or
—NR⁷R⁸,
R⁴ is H or lower alkyl,
or R³ and R⁴ together with the nitrogen atom to which they are attached form a heterocyclic ring,
R⁵ is H or lower alkyl,
R⁶ is H or lower alkyl,
R⁷ is H or lower alkyl,
R⁸ is H or lower alkyl,
Y is O or S, and
X is CH₂—O— or —CH=CH—,
or a pharmaceutically active salt or ester thereof.
2. The compound of claim 1, wherein Y is O.
3. The compound of claim 1, wherein Y is S.
4. The compound of claim 1, wherein X is —CH₂—O—.
5. The compound of claim 1, wherein X is —CH=CH—.
6. The compound of claim 1, wherein R² is lower alkyl or hydroxy-lower alkyl.
7. The compound of claim 1, wherein R² is Me or hydroxy-Me.
8. The compound of claim 1, wherein R¹ is aryl, aryl substituted by halogen, heteroaryl, or heteroaryl substituted by halogen.
9. The compound of claim 1, wherein R¹ is Ph, 4-fluoro-Ph, pyridinyl or 3-fluoro-pyridinyl.
10. The compound of claim 1, wherein R⁴ is H.
11. The compound of claim 1, wherein R³ is lower alkyl, lower alkyl substituted by hydroxyl, lower alkyl substituted by carboxy, lower alkyl substituted by halogen, heterocyclyl, or —NR⁷R⁸, wherein R⁷ and R⁸ are each independently lower alkyl.
12. The compound of claim 1, wherein R³ is 2,2,2-trifluoro-ethyl-, 2-carboxyethyl-, 2-hydroxy-1-methyl-ethyl-, 2-hydroxy-ethyl-, 3-tetrahydrofuranyl-, 4-tetrahydropuranyl-, isopropyl-, (CH$_3$)$_2$N—, piperidinyl, pyrrolidinyl or morpholino.

13. The compound of claim 1, wherein R$^3$ and R$^4$ together with the nitrogen atom to which they are attached form 2-oxa-6-aza-spiro[3.3]hept-6-yl.

14. The compound of claim 1, selected from the group consisting of
- 3-[(E)-2-(3-Butyl-5-methyl-isoxazol-4-yl)-vinyl]-isoxazole-5-carboxylic acid (2-hydroxy-ethyl)-amide,
- 3-(5-Methyl-3-phenyl-isoxazol-4-ylmethoxy)-isoxazole-5-carboxylic acid isopropylamide,
- 3-(5-Methyl-3-phenyl-isoxazol-4-ylmethoxy)-isoxazole-5-carboxylic acid (tetrahydro-furan-3-yl)-amide,
- 3-(5-Methyl-3-phenyl-isoxazol-4-ylmethoxy)-isoxazole-5-carboxylic acid (2-hydroxy-ethyl)-amide,
- 3-(5-Methyl-3-phenyl-isoxazol-4-ylmethoxy)-isoxazole-5-carboxylic acid (2-hydroxy-1-methyl-ethyl)-amide,
- Acetic acid 2-{[3-(5-methyl-3-phenyl-isoxazol-4-ylmethoxy)-isoxazole-5-carbonyl]-amino}-ethyl ester,
- 3-(5-Methyl-3-phenyl-isoxazol-4-ylmethoxy)-isoxazole-5-carboxylic acid ((S)-2-hydroxy-1-methyl-ethyl)-amide,
- 3-(5-Methyl-3-phenyl-isoxazol-4-ylmethoxy)-isoxazole-5-carboxylic acid ((R)-2-hydroxy-1-methyl-ethyl)-amide,
- 3-(5-Methyl-3-phenyl-isoxazol-4-ylmethoxy)-isoxazole-5-carboxylic acid N',N'-dimethyl-hydrazide,
- 3-(5-Methyl-3-phenyl-isoxazol-4-ylmethoxy)-isoxazole-5-carboxylic acid piperidin-1-ylamide, and
- 3-(5-Methyl-3-phenyl-isoxazol-4-ylmethoxy)-isoxazole-5-carboxylic acid pyrrolidin-1-ylamide or a pharmaceutically active salt or ester thereof.

15. The compound of claim 1, selected from the group consisting of
- 3-(5-Methyl-3-phenyl-isoxazol-4-ylmethoxy)-isoxazole-5-carboxylic acid morpholin-4-ylamide,
- 3-(5-Methyl-3-pyridin-2-yl-isoxazol-4-ylmethoxy)-isoxazole-5-carboxylic acid isopropyl amide,
- 3-(5-Methyl-3-pyridin-2-yl-isoxazol-4-ylmethoxy)-isoxazole-5-carboxylic acid (2-hydroxy-ethyl)-amide,
- 3-(5-Methyl-3-pyridin-2-yl-isoxazol-4-ylmethoxy)-isoxazole-5-carboxylic acid (tetrahydro-furan-3-yl)-amide,
- 3-(5-Methyl-3-pyridin-2-yl-isoxazol-4-ylmethoxy)-isoxazole-5-carboxylic acid (2,2,2-trifluoro-ethyl)-amide,
- 3-(5-Methyl-3-pyridin-2-yl-isoxazol-4-ylmethoxy)-isoxazole-5-carboxylic acid N',N'-dimethyl-hydrazide,
- 3-(5-Methyl-3-pyridin-2-yl-isoxazol-4-ylmethoxy)-isoxazole-5-carboxylic acid morpholin-4-ylamide,
- 3-(5-Methyl-3-pyridin-2-yl-isoxazol-4-ylmethoxy)-isoxazole-5-carboxylic acid piperidin-1-ylamide,
- 3-(5-Methyl-3-pyridin-2-yl-isoxazol-4-ylmethoxy)-isoxazole-5-carboxylic acid pyrrolidin-1-ylamide,
- 3-[3-(5-Fluoro-pyridin-2-yl)-5-methyl-isoxazol-4-ylmethoxy]-isoxazole-5-carboxylic acid isopropylamide, and
- 3-[3-(5-Fluoro-pyridin-2-yl)-5-methyl-isoxazol-4-ylmethoxy]-isoxazole-5-carboxylic acid (2-hydroxy-ethyl)-amide or a pharmaceutically active salt or ester thereof.

16. The compound of claim 1, selected from the group consisting of
- 3-(3-Butyl-5-methyl-isoxazol-4-ylmethoxy)-isoxazole-5-carboxylic acid (2-hydroxy-ethyl)-amide,
- 3-(3-Butyl-5-methyl-isoxazol-4-ylmethoxy)-isoxazole-5-carboxylic acid (2-hydroxy-1-methyl-ethyl)-amide,
- 3-(3-Butyl-5-methyl-isoxazol-4-ylmethoxy)-isoxazole-5-carboxylic acid ((S)-2-hydroxy-1-methyl-ethyl)-amide,
- 3-(3-Butyl-5-methyl-isoxazol-4-ylmethoxy)-isoxazole-5-carboxylic acid ((R)-2-hydroxy-1-methyl-ethyl)-amide,
- 3-(3-Butyl-5-methyl-isoxazol-4-ylmethoxy)-isoxazole-5-carboxylic acid isopropylamide,
- 3-(3-Butyl-5-methyl-isoxazol-4-ylmethoxy)-isoxazole-5-carboxylic acid (tetrahydro-furan-3-yl)-amide,
- 3-(3-Butyl-5-methyl-isoxazol-4-ylmethoxy)-isoxazole-5-carboxylic acid (tetrahydro-furan-3(S)-yl)-amide,
- 3-(3-Butyl-5-methyl-isoxazol-4-ylmethoxy)-isoxazole-5-carboxylic acid (tetrahydro-furan-3(R)-yl)-amide,
- 3-(3-Butyl-5-methyl-isoxazol-4-ylmethoxy)-isoxazole-5-carboxylic acid N',N'-dimethyl-hydrazide,
- 3-(3-Butyl-5-methyl-isoxazol-4-ylmethoxy)-isoxazole-5-carboxylic acid morpholin-4-ylamide, and
- 3-(5-Methyl-3-phenyl-isoxazol-4-ylmethoxy)-isothiazole-5-carboxylic acid isopropylamide or a pharmaceutically active salt or ester thereof.

17. The compound of claim 1, selected from the group consisting of
- 3-(5-Methyl-3-phenyl-isoxazol-4-ylmethoxy)-isothiazole-5-carboxylic acid (2-hydroxy-ethyl)-amide,
- 3-(5-Methyl-3-pyridin-2-yl-isoxazol-4-ylmethoxy)-isothiazole-5-carboxylic acid isopropyl amide,
- 3-(5-Methyl-3-pyridin-2-yl-isoxazol-4-ylmethoxy)-isothiazole-5-carboxylic acid (2-hydroxy-ethyl)-amide,
- 3-[3-(5-Fluoro-pyridin-2-yl)-5-methyl-isoxazol-4-ylmethoxy]-isothiazole-5-carboxylic acid isopropylamide,
- 3-[3-(5-Fluoro-pyridin-2-yl)-5-methyl-isoxazol-4-ylmethoxy]-isothiazole-5-carboxylic acid (2-hydroxy-ethyl)-amide,
- 3-[3-(5-Fluoro-pyridin-2-yl)-5-methyl-isoxazol-4-ylmethoxy]-isothiazole-5-carboxylic acid (tetrahydro-furan-3-yl)-amide,
- 3-(3-Butyl-5-methyl-isoxazol-4-ylmethoxy)-isothiazole-5-carboxylic acid (tetrahydro-furan-3-yl)-amide,
- {3-[3-(4-Fluoro-phenyl)-5-methyl-isoxazol-4-ylmethoxy]-isoxazol-5-yl}-(2-oxa-6-aza-spiro[3.3]hept-6-yl)-methanone
- 3-[3-(4-Fluoro-phenyl)-5-hydroxymethyl-isoxazol-4-ylmethoxy]-isoxazole-5-carboxylic acid isopropylamide
- 3-[3-(4-Fluoro-phenyl)-5-hydroxymethyl-isoxazol-4-ylmethoxy]-isoxazole-5-carboxylic acid (tetrahydro-pyran-4-yl)-amide, and
- 3-[3-(4-Fluoro-phenyl)-5-hydroxymethyl-isoxazol-4-ylmethoxy]-isoxazole-5-carboxylic acid (2,2,2-trifluoro-ethyl)-amide or a pharmaceutically active salt or ester thereof.

18. A compound of claim 1, selected from the group consisting of
- 3-(5-Methyl-3-phenyl-isoxazol-4-ylmethoxy)-isoxazole-5-carboxylic acid isopropylamide,
- 3-(5-Methyl-3-phenyl-isoxazol-4-ylmethoxy)-isoxazole-5-carboxylic acid (tetrahydro-furan-3-yl)-amide,
- 3-(5-Methyl-3-phenyl-isoxazol-4-ylmethoxy)-isoxazole-5-carboxylic acid (2-hydroxy-ethyl)-amide,
- 3-(5-Methyl-3-phenyl-isoxazol-4-ylmethoxy)-isoxazole-5-carboxylic acid (2-hydroxy-1-methyl-ethyl)-amide,
- Acetic acid 2-{[3-(5-methyl-3-phenyl-isoxazol-4-ylmethoxy)-isoxazole-5-carbonyl]-amino}-ethyl ester,
- 3-(5-Methyl-3-phenyl-isoxazol-4-ylmethoxy)-isoxazole-5-carboxylic acid ((S)-2-hydroxy-1-methyl-ethyl)-amide,
- 3-(5-Methyl-3-phenyl-isoxazol-4-ylmethoxy)-isoxazole-5-carboxylic acid piperidin-1-ylamide, 3-(5-Methyl-3-phenyl-isoxazol-4-ylmethoxy)-isoxazole-5-carboxylic acid pyrrolidin-1-ylamide, and
3-(5-Methyl-3-phenyl-isoxazol-4-ylmethoxy)-isoxazole-5-carboxylic acid morpholin-4-ylamide,
or a pharmaceutically active salt or ester thereof.

19. A compound of claim 1, selected from the group consisting of
3-(5-Methyl-3-pyridin-2-yl-isoxazol-4-ylmethoxy)-isoxazole-5-carboxylic acid isopropyl amide,
3-(5-Methyl-3-pyridin-2-yl-isoxazol-4-ylmethoxy)-isoxazole-5-carboxylic acid (2-hydroxy-ethyl)-amide,
3-(5-Methyl-3-pyridin-2-yl-isoxazol-4-ylmethoxy)-isoxazole-5-carboxylic acid (tetrahydro-furan-3-yl)-amide,
3-(5-Methyl-3-pyridin-2-yl-isoxazol-4-ylmethoxy)-isoxazole-5-carboxylic acid (2,2,2-trifluoro-ethyl)-amide,
3-(5-Methyl-3-pyridin-2-yl-isoxazol-4-ylmethoxy)-isoxazole-5-carboxylic acid N',N'-dimethyl-hydrazide,
3-(5-Methyl-3-pyridin-2-yl-isoxazol-4-ylmethoxy)-isoxazole-5-carboxylic acid morpholin-4-ylamide,
3-(5-Methyl-3-pyridin-2-yl-isoxazol-4-ylmethoxy)-isoxazole-5-carboxylic acid piperidin-1-ylamide,
3-(5-Methyl-3-pyridin-2-yl-isoxazol-4-ylmethoxy)-isoxazole-5-carboxylic acid pyrrolidin-1-ylamide, and
3-[3-(5-Fluoro-pyridin-2-yl)-5-methyl-isoxazol-4-ylmethoxy]-isoxazole-5-carboxylic acid isopropylamide
or a pharmaceutically active salt or ester thereof.

20. A compound of claim 1, selected from the group consisting of
3-[3-(5-Fluoro-pyridin-2-yl)-5-methyl-isoxazol-4-ylmethoxy]-isoxazole-5-carboxylic acid (2-hydroxy-ethyl)-amide,
3-(3-Butyl-5-methyl-isoxazol-4-ylmethoxy)-isoxazole-5-carboxylic acid (tetrahydro-furan-3-yl)-amide,
3-(3-Butyl-5-methyl-isoxazol-4-ylmethoxy)-isoxazole-5-carboxylic acid (tetrahydro-furan-3(R)-yl)-amide,
3-(3-Butyl-5-methyl-isoxazol-4-ylmethoxy)-isoxazole-5-carboxylic acid (tetrahydro-furan-3(S)-yl)-amide,
3-(3-Butyl-5-methyl-isoxazol-4-ylmethoxy)-isoxazole-5-carboxylic acid morpholin-4-ylamide,
3-(5-Methyl-3-pyridin-2-yl-isoxazol-4-ylmethoxy)-isothiazole-5-carboxylic acid isopropyl amide,
3-(5-Methyl-3-pyridin-2-yl-isoxazol-4-ylmethoxy)-isothiazole-5-carboxylic acid (2-hydroxy-ethyl)-amide,
3-[3-(5-Fluoro-pyridin-2-yl)-5-methyl-isoxazol-4-ylmethoxy]-isothiazole-5-carboxylic acid isopropylamide,
3-[3-(5-Fluoro-pyridin-2-yl)-5-methyl-isoxazol-4-ylmethoxy]-isothiazole-5-carboxylic acid (2-hydroxy-ethyl)-amide, and
3-[3-(5-Fluoro-pyridin-2-yl)-5-methyl-isoxazol-4-ylmethoxy]-isothiazole-5-carboxylic acid (tetrahydro-furan-3-yl)-amide,
or a pharmaceutically active salt or ester thereof.

21. A compound of claim 1, selected from the group consisting of
3-(5-Methyl-3-pyridin-2-yl-isoxazol-4-ylmethoxy)-isoxazole-5-carboxylic acid (tetrahydro-furan-3-yl)-amide,
3-[3-(5-Fluoro-pyridin-2-yl)-5-methyl-isoxazol-4-ylmethoxy]-isoxazole-5-carboxylic acid isopropylamide,
3-(5-Methyl-3-pyridin-2-yl-isoxazol-4-ylmethoxy)-isoxazole-5-carboxylic acid morpholin-4-ylamide,
3-[3-(5-Fluoro-pyridin-2-yl)-5-methyl-isoxazol-4-ylmethoxy]-isoxazole-5-carboxylic acid (2-hydroxy-ethyl)-amide,
3-(5-Methyl-3-pyridin-2-yl-isoxazol-4-ylmethoxy)-isoxazole-5-carboxylic acid (2,2,2-trifluoro-ethyl)-amide,
3-(5-Methyl-3-pyridin-2-yl-isoxazol-4-ylmethoxy)-isoxazole-5-carboxylic acid isopropyl amide,
3-(5-Methyl-3-phenyl-isoxazol-4-ylmethoxy)-isoxazole-5-carboxylic acid morpholin-4-ylamide,
3-(3-Butyl-5-methyl-isoxazol-4-ylmethoxy)-isoxazole-5-carboxylic acid (tetrahydro-furan-3(S)-yl)-amide,
3-(5-Methyl-3-pyridin-2-yl-isoxazol-4-ylmethoxy)-isoxazole-5-carboxylic acid (2-hydroxy-ethyl)-amide,
3-[3-(5-Fluoro-pyridin-2-yl)-5-methyl-isoxazol-4-yl-methoxy]-isothiazole-5-carboxylic acid (tetrahydro-furan-3-yl)-amide,
3-(5-Methyl-3-phenyl-isoxazol-4-ylmethoxy)-isoxazole-5-carboxylic acid (tetrahydro-furan-3-yl)-amide,
3-(5-Methyl-3-pyridin-2-yl-isoxazol-4-ylmethoxy)-isoxazole-5-carboxylic acid piperidin-1-ylamide, and
3-(3-Butyl-5-methyl-isoxazol-4-ylmethoxy)-isoxazole-5-carboxylic acid (tetrahydro-furan-3(R)-yl)-amide,
or a pharmaceutically active salt or ester thereof.

22. A pharmaceutical composition comprising a therapeutically effective amount of a compound of formula I

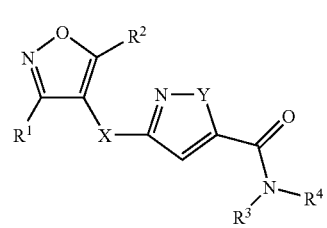

$R^1$ is lower alkyl, optionally substituted by halogen, cyano, hydroxy, lower-alkoxy or halogen-lower-alkoxy,
aryl, heteroaryl, cycloalkyl, or heterocyclyl; each of which is optionally substituted by halogen, cyano, hydroxy, lower alkyl, halogen-lower alkyl, cyano-lower alkyl, hydroxy-lower alkyl, lower alkyl-C(=O)OH, lower alkyl-C(=O)O-lower alkyl, lower alkyl-CO—$NR^5R^6$, lower alkyl-$NR^5R^6$, lower-alkoxy-lower alkyl, —CO-lower alkyl, —C(=O)OH, —C(=O)O-lower alkyl, —CONR$^5$R$^6$, —NR$^5$R$^6$, lower-alkoxy, halogen-lower-alkoxy, —SO$_2$-lower alkyl, —SO$_2$—NR$^5$R$^6$, cycloalkyl, phenyloxy or phenyl,
$R^2$ is lower alkyl optionally substituted by halogen, cyano, hydroxy, lower-alkoxy or halogen-lower-alkoxy,
$R^3$ is lower alkyl, optionally substituted by carboxy, halogen or hydroxyl;
aryl, heteroaryl, cycloalkyl, or heterocyclyl; each of which is optionally substituted by carboxy, halogen, hydroxy or lower alkyl; or
—NR$^7$R$^8$,
$R^4$ is H or lower alkyl, or $R^3$ and $R^4$ together with the nitrogen atom to which they are attached form a heterocyclic ring,
$R^5$ is H or lower alkyl,
$R^6$ is H or lower alkyl,
$R^7$ is H or lower alkyl,
$R^8$ is H or lower alkyl,
Y is O or S, and
X is CH$_2$—O— or —CH=CH—,
or pharmaceutically active salt or ester thereof and a pharmaceutically acceptable carrier.

* * * * *